(12) United States Patent
Nambu et al.

(10) Patent No.: US 7,826,885 B2
(45) Date of Patent: Nov. 2, 2010

(54) METHOD AND APPARATUS FOR CALCULATING INDEX CONCERNING LOCAL BLOOD FLOW CIRCULATIONS

(75) Inventors: Kyojiro Nambu, Nasu-gun (JP); Yoshihiro Ikeda, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 219 days.

(21) Appl. No.: 11/855,195

(22) Filed: Sep. 14, 2007

(65) Prior Publication Data
US 2008/0075344 A1 Mar. 27, 2008

Related U.S. Application Data

(62) Division of application No. 10/269,960, filed on Oct. 15, 2002.

(30) Foreign Application Priority Data

| Oct. 16, 2001 | (JP) | ............................. 2001-318344 |
| Oct. 16, 2001 | (JP) | ............................. 2001-318345 |
| Sep. 27, 2002 | (JP) | ............................. 2002-284450 |

(51) Int. Cl.
*A61B 5/05* (2006.01)

(52) U.S. Cl. ....................... 600/407; 600/408; 600/410; 600/424; 600/425; 378/4; 378/8; 378/19

(58) Field of Classification Search ................. 600/407, 600/408, 410–423; 378/4, 8, 19
See application file for complete search history.

(56) References Cited

U.S. PATENT DOCUMENTS 4,718,432 A 1/1988 Kimura et al.

(Continued)

FOREIGN PATENT DOCUMENTS

EP 1 114 615 7/2001

(Continued)

OTHER PUBLICATIONS

R. Takehara, et al., "Quantitative Measurement of Cerebral Blood Flow by Dynamic CT", Proceedings of the XV Symposium Neuroradiologicum, Kumamoto, Sep. 25-Oct. 1, 1994, pp. 580-583.

(Continued)

*Primary Examiner*—Brian Casler
*Assistant Examiner*—John F Ramirez
(74) *Attorney, Agent, or Firm*—Oblon, Spivak, McClelland, Maier & Neustadt, L.L.P.

(57) ABSTRACT

First time-density curves concerning arteries in a specific region and second time-density curves concerning tissues in the specific region are prepared from a plurality of continuous images concerning the specific region of a subject into which a contrast medium is injected. Modulation transfer functions indicating local blood flow circulations in the tissues with respect to the arteries are calculated by curve-fitting so that residual errors of the second time-density curves are minimized with respect to convolution of the modulation transfer functions and first time-density curves. Indices concerning the local blood flow circulations with respect to the respective arteries are calculated from the modulation transfer functions. Maps of the indices for the arteries are prepared, and the maps of these indices are synthesized into one map in accordance with the residual errors for the first time-density curves.

7 Claims, 19 Drawing Sheets

U.S. PATENT DOCUMENTS

| | | |
|---|---|---|
| 4,793,358 A | 12/1988 | Kimura et al. |
| 4,939,757 A | 7/1990 | Nambu |
| 5,018,173 A | 5/1991 | Komai et al. |
| 6,005,917 A | 12/1999 | Andersson et al. |
| 6,196,715 B1 | 3/2001 | Nambu et al. |
| 6,512,807 B1 | 1/2003 | Pohlman et al. |
| 6,542,769 B2 | 4/2003 | Schwamm et al. |
| 7,069,068 B1 | 6/2006 | Ostergaard |

FOREIGN PATENT DOCUMENTS

| | | |
|---|---|---|
| JP | 63-177837 | 7/1988 |
| JP | 63-242226 | 10/1988 |
| JP | 2000-50109 | 2/2000 |
| JP | 2000-237194 | 9/2000 |
| JP | 2001-61157 | 3/2001 |
| JP | 2001-212115 | 8/2001 |
| WO | WO 98/32376 | 7/1998 |
| WO | WO 00/57777 | 10/2000 |
| WO | WO 00/74572 A1 | 12/2000 |

OTHER PUBLICATIONS

K. Nambu, et al., "A Method of Regional Cerebral Blood Perfusion Measurement Using Dynamic CT With an Iodinated Contrast Medium", Acta Neurologica Scandinavica, Third International Conference on Xenon/CT CBF Jun. 25-28, 1995, Supplementum No. 166, vol. 93, 1996, pp. 28-31.

B. Schrope, et al., Ultrasonic Imaging, vol. 14, No. 2, XP-000270104, pp. 134-158, "Simulated Capillary Blood Flow Measurement Using a Nonlinear Ultrasonic Contract Agent" Apr. 1, 1992.

C.J. Wolfkiel, et al., IEEE Transactions on Biomedical Engineering, vol. 41, No. 1, XP-000448136, pp. 69-76, "Transfer-Function Analysis of UFCT Myocardial Time-Density Curves by Time-Varying Recursive Least Squares Analysis", 1994.

Thomas Ernst, et al., "Correlation of Regional Cerebral Blood Flow From Perfusion MRI and Spect in Normal Subjects", Magnetic Resonance Imaging, XP-002359211, vol. 17, No. 3, Apr. 1999, pp. 349-354.

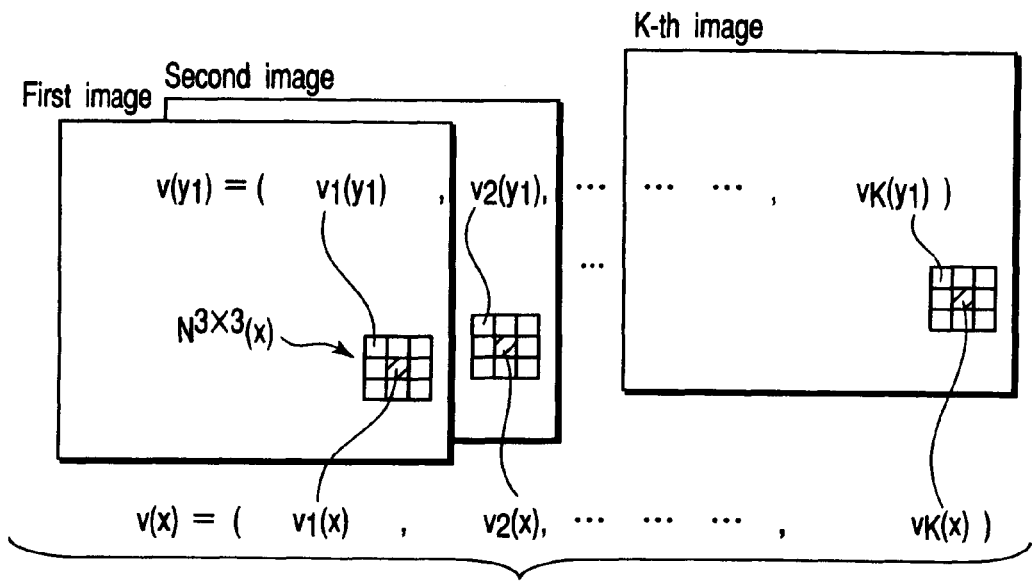
FIG. 3A
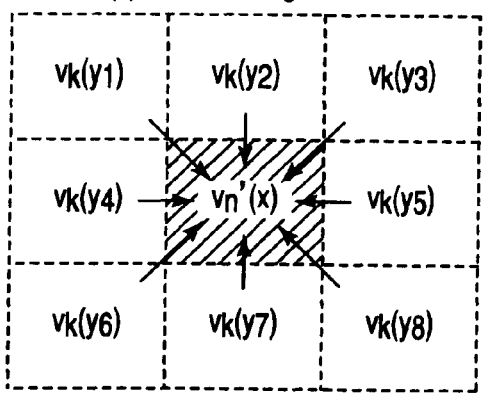
FIG. 3B
FIG. 3C
With respect to each of K still images in the drawing
$$w1(p(x,y)) = \exp\left[-\left\{\frac{\sqrt{\sum_{k=1}^{k}\frac{\{V_k(x)-V_k(y)\}^2}{K}}}{2\sigma}\right\}^C\right]$$
$$v'_k(x) = \frac{\sum_{y \in (y_1,\cdots,y_8,x)} V_k(y) \cdot w1(p(x,y))}{\sum_{y \in (y_1,\cdots,y_8,x)} w1(p(x,y))}$$

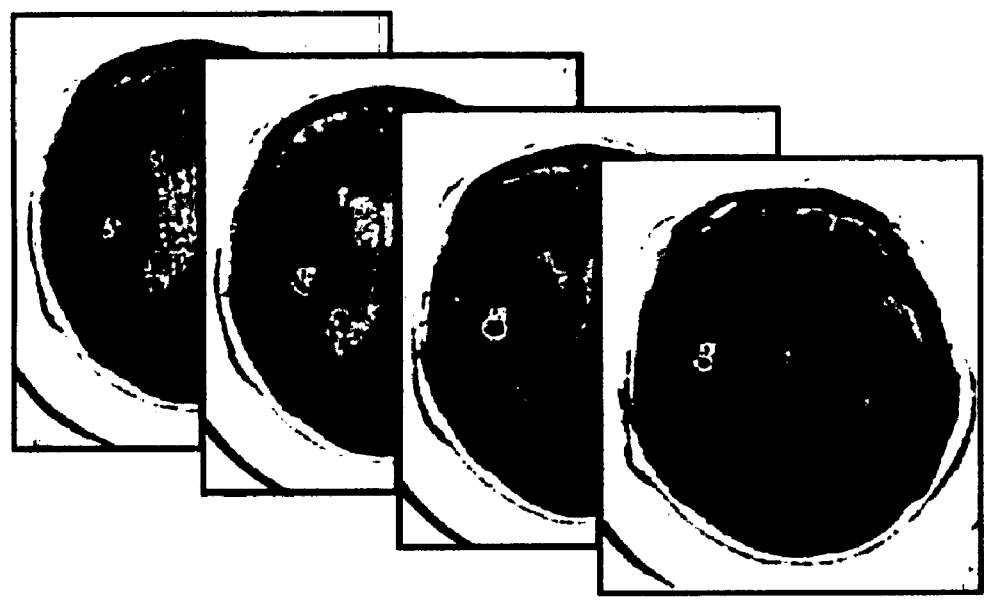
F I G. 11
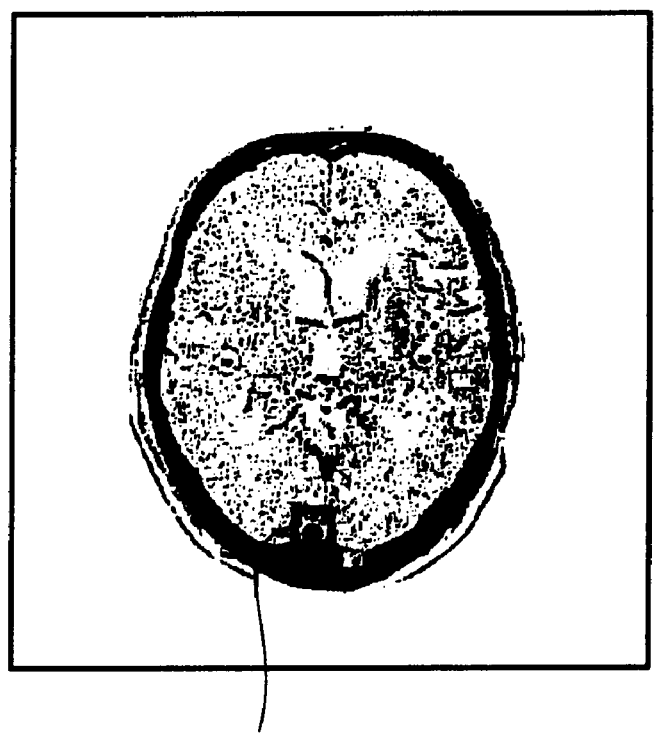
Upper sagittal sinus venosus ROI
F I G. 12

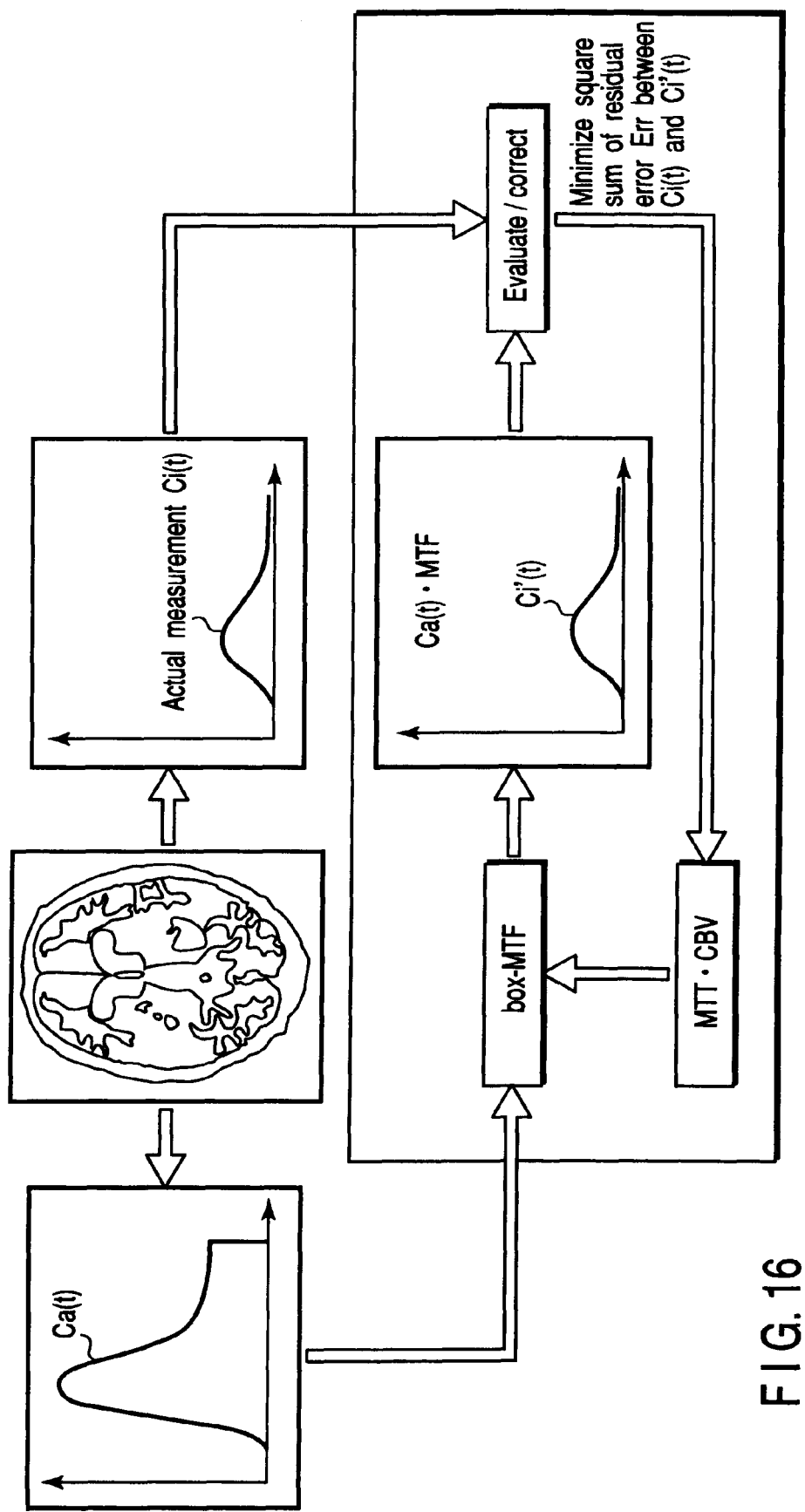
F I G. 16

| box-MTF | | | | | |
|---|---|---|---|---|---|
| Range of output result | | | Conversion magnification to pixel value | | |
| | Lower limit | Upper limit | Unit | | |
| ☐ CBP | 0.0 | 90.0 | ml/100cc/min X | 10 | |
| ☐ CBV | 0.0 | 8.0 | % X | 100 | |
| ☐ mtt | 1.6 | 9999.0 | sec X | 100 | |
| ☐ Err | | 1.0 | H.U. X | 1000 | |

When analysis result exceeds the above range, display turns black (to −2051)

[ OK ]     [ Cancel ]

FIG. 17

CBP

CBV

MTT

Err

CBP map
F I G. 21A
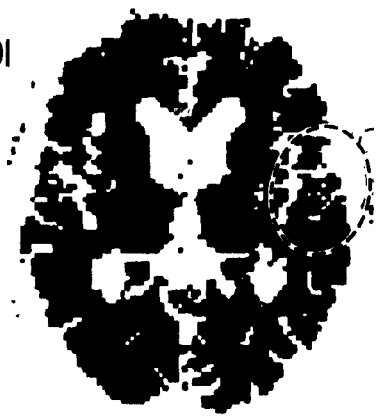
CBV map
F I G. 21B
MTT map
F I G. 21C
Err map
F I G. 21D 1 : Pixel in which Err of right ACA is minimum
2 : Pixel in which Err of right MCA is minimum
3 : Pixel in which Err of right PCA is minimum
4 : Pixel in which Err of left ACA is minimum
5 : Pixel in which Err of left MCA is minimum
6 : Pixel in which Err of left PCA is minimum

METHOD AND APPARATUS FOR CALCULATING INDEX CONCERNING LOCAL BLOOD FLOW CIRCULATIONS

CROSS-REFERENCE TO RELATED APPLICATIONS

The present divisional application claims the benefit of priority under 35 U.S.C. §120 to application Ser. No. 10/269,960, filed Oct. 15, 2002, and under 35 U.S.C. §119 from the prior Japanese Patent Applications No. 2001-318344, filed Oct. 16, 2001; No. 2001-318345, filed Oct. 16, 2001; and No. 2002-284450, filed Sep. 27, 2002, the entire contents of each are incorporated herein by reference.

BACKGROUND OF THE INVENTION

1. Field of the Invention

The present invention relates to a calculation method and apparatus of an index concerning local blood flow circulations in cerebral tissues.

2. Description of the Related Art

In X-ray CT inspection, configuration information from a simple CT image, and circulation information of blood flow around a seat of disease in a dynamic scan by contrast CT can be obtained as visual information. In recent years, a high-speed scan by multislice CT has been possible and it is considered that a utilization range of the dynamic scan of contrast CT is increasingly enlarged.

As one directionality, there is a method called a CBP study for calculating an index concerning blood flow circulations of capillaries in cerebral tissues. The CBP study comprises: obtaining indices such as CBP, CBV, MTT, and Err quantitatively indicating local blood flow circulations in the tissues, that is, the circulations of the blood flow through the capillaries in the local tissues; and outputting maps of these indices.

CBP denotes blood flow rate [ml/100 ml/min] per unit volume and time in the capillaries for the cerebral tissues; CBV denotes a blood volume [ml/100 ml] per unit volume in the cerebral tissues; MTT denotes a blood mean transit time [second] of the capillaries; and Err denotes a sum of residual errors or square root of the sum of squares of the residual errors in approximation of a modulation transfer function.

The indices CBP, CBV, MTT quantitatively indicating the blood flow circulations of the capillaries in the cerebral tissues, together with transit time information after development of cerebral ischemia apoplexy, are expected as useful information for differentiating a disease body of ischemic cerebral vascular disorder, judging the presence/absence of enlargement of the capillaries, or evaluating blood flow rate. For example, in general, in ischemic cerebral vascular disorders, blood pressure of a provided artery drops, and the intravascular blood flow rate drops. As a result, even when the CBV is constant, MTT extends, and CBP drops. Moreover, in a cerebral infarction hyperacute stage, to compensate for the drop of the blood flow rate by the blood pressure drop, there is an autoregulation for expanding the capillaries, increasing the blood flow rate CBP. Therefore, since the MTT extends, even with the drop of the CBP, with the increase of the CBV, the information implies a possibility of revascularization of the capillaries.

In the CBP study, a contrast medium having no cerebral vessel permeability, such as an iodinated contrast medium, is used as a tracer. The iodinated contrast medium is injected via a cubital vein, for example, by an injector. The iodinated contrast medium injected into the vein by the injector flows into a cerebral artery via heart and lung. Then, the contrast medium flows out to the cerebral veins from the cerebral arteries through the capillaries in the cerebral tissues. The iodinated contrast medium passes through the capillaries in normal cerebral tissues without any extravascular leakage. FIG. 1 schematically shows this state.

The state of passage of the contrast medium is scanned by dynamic CT, and a time-density curve $Ca(t)$ of a pixel on the cerebral artery, time-density curve $Ci(t)$ of the pixel on the cerebral tissue (capillary), and time-density curve $Csss(t)$ of the pixel on the cerebral vein are measured from a continuous image.

Here, in the CBP study, an ideal relation established between the time-density curve $Ca(t)$ of the cerebral artery and the time-density curve $Ci(t)$ of the cerebral tissue is used as an analysis model. Assuming if the contrast medium is injected via the vessel immediately before the cerebral tissue, the time-density curve in the unit volume (one pixel) for the cerebral tissue rides vertically, holds a constant value for a while, and thereafter falls steeply. This is approximated with a rectangular function (box-modulation transfer function method: box-MTF method).

That is, the time-density curve $Ca(t)$ of the cerebral artery is used as an input function, the time-density curve $Ci(t)$ for the cerebral tissue is used as an output function, and a modulation transfer function between the input and output functions is approximated by a rectangular function. The modulation transfer function indicates a process of passage of the tracer through the capillary.

The CBP study has the following problems.

Since the respective indices of the CBP, CBV, MTT, and Err are calculated for each pixel (x,y,z), an image using the value as the pixel value can be constituted, and this image is referred to as a map. For example, when R types of indices are obtained, R maps can be constituted. The R maps prepared in this manner can be regarded as one map (vector value map) in which each pixel has a vector value. That is, the map can be represented as follows.

$$V_k(x,y,z) = <P_{k,1}(x,y,z), P_{k,2}(x,y,z), \ldots, P_{k,R}(x,y,z)>$$

For example, the CBP study can be constituted in such a manner that typically R=4 is assumed, $P_{k,1}(x,y,z)$ indicates the value of CBP, $P_{k,2}(x,y,z)$ indicates the value of CBV, $P_{k,3}(x,y,z)$ indicates the value of MTT, and $P_{k,4}(x,y,z)$ indicates the value of a residual errors error Err.

This vector value map $V_k$ is prepared for each time-density curve $Ca(t)_k$ of the referred cerebral artery. For example, assuming that the time-density curves of the cerebral arteries are obtained from medial, anterior and posterior cerebral arteries in left and right hemispheres. In this case, K=6. Furthermore, assuming that the time-density curve of the cerebral artery is obtained from artery several portions in the periphery of an affected area, K=about 10 to 15.

When the number K of the time-density curve $Ca(t)_k$ of the cerebral artery is large (k=1, 2, . . . , K), the number of vector value maps $V_k$ (k=1, 2, . . . , K) obtained as a result is large, and this is therefore inconvenient for observation. That is, when the map is to be observed as a usual gray scale image or color scale image, one map is constituted of R images, there are K maps, and therefore K×R images in total have to be compared. Furthermore, the area nourished by an artery and the artery are not necessarily apparent, and an anatomical knowledge is necessary to judge the map $V_k$ (k=1, 2, . . . , K) to be observed for each area. Particularly, in the development of the cerebral vascular disorder such as the cerebral infarction, the judgment of the artery which depends on the tissue may not agree with the anatomical knowledge, and abnormal dependence is frequently seen. These problems raise a problem that it is difficult to interpret radiogram of the vector value map.

Moreover, in the dynamic CT image scanned by multi-slice or volume CT, a large number of arteries are further observed. This is because the same artery can be observed in a plurality of slices. If the time-density curve of the cerebral artery is prepared for all tomography images of these arteries, the number of curves becomes very large.

Furthermore, the CBP study also has the following problems. With bolus injection via the cubital vein, for a contrast enhancement effect observed with the CT, the CT number of blood rises to several hundreds of HU at maximum (several tens of HU, when contrast imaging is not performed). However, to effectively analyze the cerebral blood flow, a contrast enhancement effect has to be measured only with an error of several percentages or less. That is, even when the contrast enhancement effect (the rise of CT number) is about 20 to 40 HU, the contrast enhancement effect has to be detected.

A volume ratio of capillaries in the cerebral tissue of a unit volume is about 3 to 4% at maximum. Therefore, when the CT number of blood rises by 20 to 40 HU, a mean CT number for the cerebral tissue only rises by about 0.5 to 1.5 HU.

In the CT image, a standard deviation (sd) of noise is in inverse proportion to a square root of an X ray radiation dose, and sd is, for example, about 5 to 10 HU in typical irradiation conditions. Therefore, to detect the contrast enhancement effect of 0.5 HU, the X ray radiation dose has to be increased by about 10 to 100 times, and this means that an exposed dose of a patient is remarkably large. Moreover, since the same position is scanned several tens of times in the dynamic CT, exposure of skin in the scanned position reaches several hundreds to thousands of times the normal exposure, and this is not realistic in consideration of radiation troubles such as inflammation, alopecia, necrosis, and carcinogenesis.

Rather in the dynamic CT, the X ray radiation dose has to be decreased as compared with the usual scanning. In general, the X ray radiation dose per scan is reduced, for example, to about ½ to ¹⁄₁₀ of a usual dose. Thereby, about several to 20 times the X-ray exposure can only result as compared with usual one CT scanning, and any radiation trouble does not occur. However, in the CT image in which the X ray radiation dose is reduced, sd is, for example, about 15 to 20 HU, and the contrast enhancement effect of about 0.5 to 1.5 HU can hardly be detected.

Therefore, to suppress noise components of the image is one of important problems in the CBP study. For this, 1) to increase a slice thickness, 2) to average adjacent pixels, and 3) to subject the image to a smoothing processing are general measures to be taken. However, these have the following problem.

In order to "increase the slice thickness", the slice thickness is set to be large during the scan, or the number of images of continuous thin slices is averaged and the image of a thick slice is generated. Since the X ray radiation dose per pixel increases in proportion to the slice thickness, sd of the image noise decreases in inverse proportion to the square root of the slice thickness. However, when the slice thickness is increased, a partial volume effect is produced. That is, one pixel does not show a uniform cerebral tissue, a probability that the pixel shows the mean CT number of a plurality of tissues (white matter, gray matter, blood vessel, cerebral sulci, cerebral ventricles, and the like) is incorrect, and the value of the cerebral blood flow rate obtained as the analysis result becomes incorrect.

Particularly, it is impossible to normally analyze the pixel including the influence of the vessel. Therefore, with the increased slice thickness, only a very low-quality result including a large number of pixels which cannot be analyzed is obtained.

Averaging the adjacent pixels, the spatial resolution is sacrificed to some degree. For example, a mean value of square regions (including n×n pixels) whose one side includes n pixels is obtained as a mean CT number of the whole square, this square is regarded as the pixel, and the squares are arranged to constitute a "pixel bundled image". For example, assuming that the original image includes 512 pixels in one side (including 512×512 images), and n=2, the "pixel bundled image" is constituted of (512/2) pixels in one side (the image includes 256×256 pixels). According to the method, the noise can be reduced in inverse proportion to n. Furthermore, the number of pixels as analysis objects increases by a factor of 1/(n×n), and therefore there is an advantage that a calculation amount is also reduced.

However, when n is increased, the spatial resolution drops, and accordingly the partial volume effect occurs. That is, one pixel does not show uniform cerebral tissue, the probability that the pixel shows the mean CT number of a plurality of tissues (white matter, gray matter, blood vessel, cerebral sulci, cerebral ventricles, and the like) becomes incorrect, and the value of the cerebral blood flow rate obtained as the analysis result becomes incorrect. Particularly, it is impossible to normally analyze the pixel including the influence of the vessel. Therefore, with the increased n, the spatial resolution is low, and only the incorrect and very low-quality result including a large number of pixels which cannot be analyzed is obtained. Therefore, in practical use, n=about 2 to 4 is a limitation, and a sufficient noise suppressing effect cannot be obtained only with this measure.

Moreover, when the image is smoothed, that is, a method of operating a two-dimensional spatial filter for each CT image and smoothing the image is used, the sufficient noise suppressing effect is obtained, but the spatial resolution is remarkably impaired. Particularly, the pixel in the vicinity of a region in which thick vessels (arteries/veins) exist is influenced by the contrast enhancement effect generated in the thick vessels, and the time-density curve of these pixels is not correct. Therefore, the smoothing has to be only slightly performed. Here, in performing only the slight smoothing, it is important to remarkably reduce the size of the image filter, for example, to about 3×3. When the 3×3 smoothing filter is used to obtain a maximum image noise suppressing effect, an upper limitation is to reduce the noise sd to ⅓, and it is impossible to further suppress the noise. Therefore, a sufficient noise suppressing effect cannot be obtained.

On the other hand, when smoothing along time axis, that is, a method of regarding the time-density curve obtained for each pixel as a curve and smoothing the curve with one-dimensional filter is used, and the sufficient noise suppressing effect is obtained, the time resolution is remarkably impaired. In the CBP study, the dynamic CT is originally performed in order to obtain a high time resolution by performing scanning in a short sampling cycle and to precisely measure a slight and rapid change (degree of a smoothing effect resulting particularly from a physiologic structure) of the time-density curve, and the smoothing with time is not appropriate.

BRIEF SUMMARY OF THE INVENTION

An object of the present invention is to enhance a diagnosis efficiency of a map obtained by a CBP study.

Another object of the present invention is to suppress noise without decrease of spatial and time resolution, and thereby enhance an analysis precision of the CBP study.

According to a first aspect of the present invention, there is provided a method of: preparing first time-density curves concerning arteries in a specific region and second time-density curves concerning tissues in the specific region from a plurality of continuous images concerning the specific region of a subject with a contrast medium injected therein; calculating modulation transfer functions indicating local blood flow circulations in the tissues with respect to the arteries by curve-fitting so that residual errors of the second time-density curves are minimized with respect to convolution of the modulation transfer functions and first time-density curves; calculating indices concerning the local blood flow circulations with respect to the respective arteries from the modulation transfer functions; preparing maps of the indices for the arteries; and synthesizing the maps of the indices into one map in accordance with the residual errors for the first time-density curves.

According to a second aspect of the present invention, there is provided a method of: preparing first time-density curves concerning arteries in a specific region and second time-density curves concerning tissues in the specific region from a plurality of continuous images concerning the specific region of a subject with a contrast medium injected therein; selecting one of the first time-density curves most fitting the respective second time-density curves to specify one of the arteries having a highest possibility that a local blood flow circulation of each in the tissues is dependent; and preparing a map to distinguish a dependent region of the artery based on one artery specified for each tissue.

According to a third aspect of the present invention, there is provided a method of: using a weight in accordance with similarity between pixels to filter a plurality of images in order to reduce noise from the plurality of continuous images concerning a specific region of a subject with a contrast medium injected therein; preparing first time-density curves concerning arteries in the specific region and second time-density curves concerning tissues in the specific region from the plurality of images with the reduced noise; calculating modulation transfer functions indicating local blood flow circulations in the tissues with respect to the respective arteries by curve-fitting so that residual errors of the second time-density curves are minimized with respect to convolution of the modulation transfer functions and first time-density curves; and calculating indices concerning the local blood flow circulations with respect to the respective arteries from the modulation transfer functions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 3A, 3B, 3C are explanatory views of an image processing by a coherent filter of the present embodiment;

FIG. 11 is a diagram showing a cerebral artery ROI which is common among slices in step S6 of FIG. 5;

FIG. 12 is a diagram showing an upper sagittal sinus venosus ROI set in step S7 of FIG. 5;

FIG. 16 is an explanatory view of a box-MTF processing of the step S12 of FIG. 6;

FIG. 17 is a diagram showing one example of an output range setting screen of each index of step S14 of FIG. 6;

FIGS. 21A to 21D are diagrams showing display examples of a mean value calculated in step S19 of FIG. 6;

DETAILED DESCRIPTION OF THE INVENTION

A preferred embodiment of the present invention will be described hereinafter with reference to the drawings.

Characteristics of the present embodiment lie in a method of: synthesizing many index maps generated by a CBP study into one map, so that diagnosis efficiency of the CBP study is enhanced; and further using a coherent filter to establish both reduction of noise and inhibition of drop of space and time resolutions so that precision of an index is enhanced.

Furthermore, the present embodiment relates to a method and apparatus in which an index indicating a local blood flow circulation is calculated from a plurality of images concerning a specific region of a subject and continuous with time, and a modality generating the plurality of images as objects is not limited to a specific apparatus. Examples of the apparatus include an X-ray computer tomography apparatus (X-ray CT apparatus), single photon emission tomography apparatus (SPECT), positron emission tomography apparatus (PET), and magnetic resonance imaging apparatus (MRI). Here, the X-ray CT apparatus will be described as an example.

(Apparatus Constitution)

Figure 1:
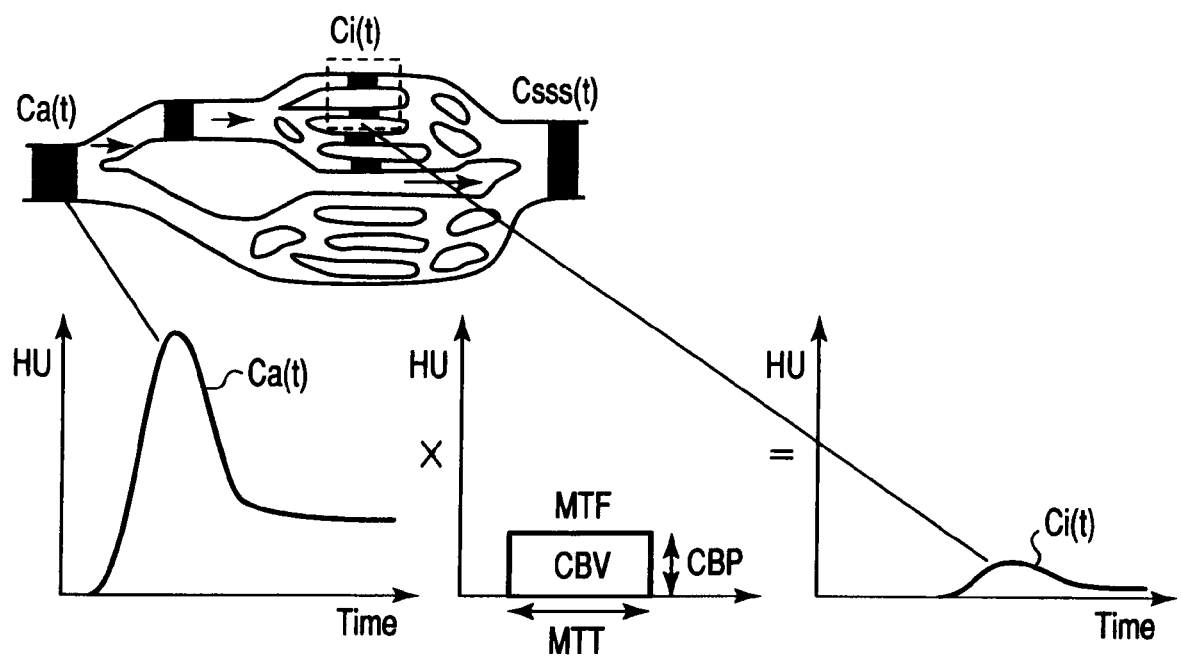
FIG. 1 is a principle explanatory view of a CBP study.
Figure 2:
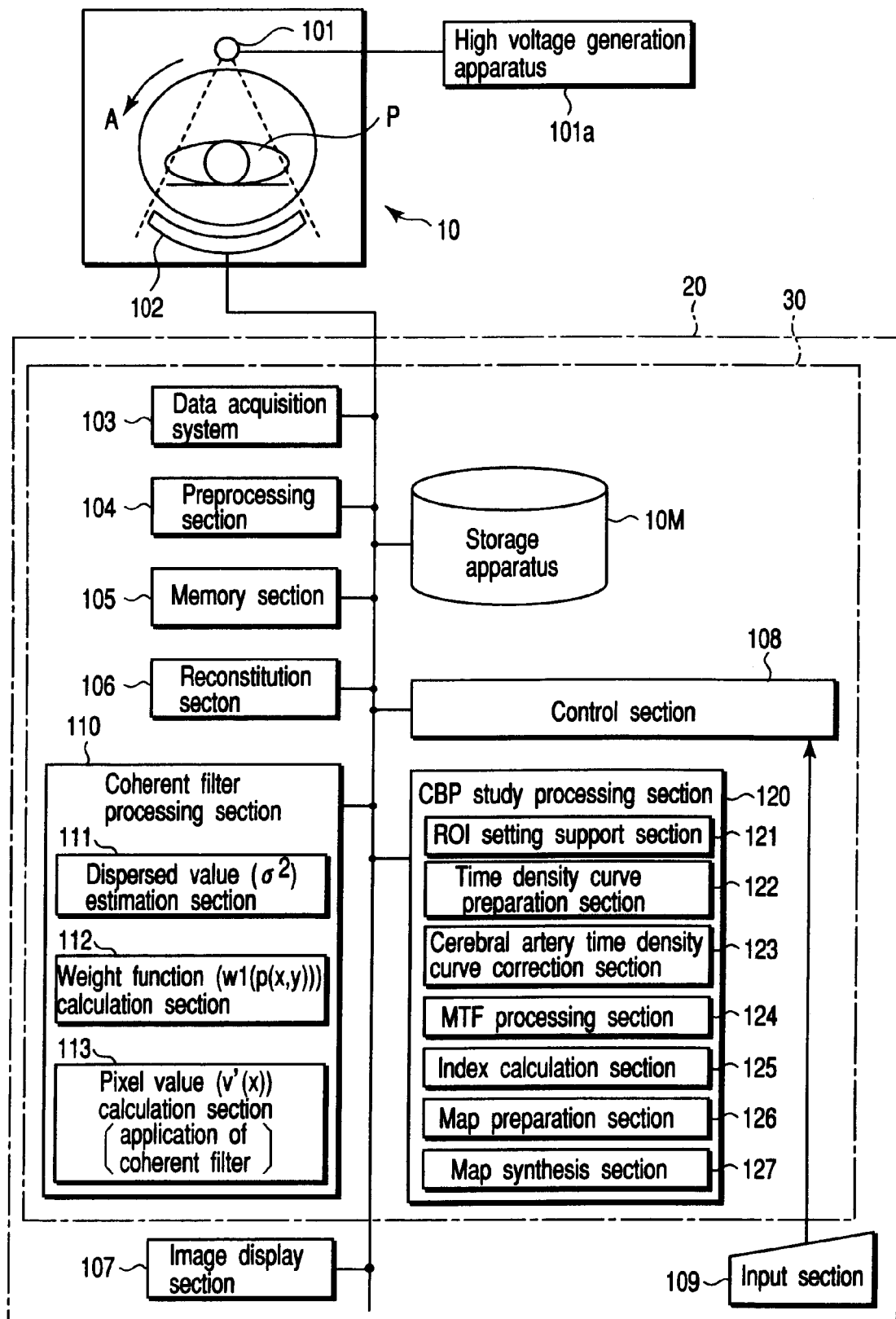
FIG. 2 is a block diagram showing a constitution of an index calculation apparatus concerning blood flow circulations of capillaries in cerebral tissues according to an embodiment of the present invention.

FIG. 2 shows a constitution of the X-ray CT apparatus according to the present embodiment. The X-ray CT apparatus is constituted of a gantry section 10 and computer apparatus 20. The gantry section 10 includes an X-ray tube 101, high voltage generation apparatus 101a, X-ray detector 102, and data acquisition system (DAS) 103. The X-ray tube 101 and X-ray detector 102 are disposed opposite to each other via a subject P on a rotary ring (not shown) which continuously rotates at a high speed.

The computer apparatus 20 includes an image processing apparatus 30, image display section 107, and input section 109. The image processing apparatus 30 includes a control section 108 as a central unit, and further includes: a preprocessing section 104 for converting raw data output from the data acquisition system 103 to projection data through a correction processing; a memory section 105 for storing the projection data; an image reconstitution section 106 for reconstituting CT image data from the projection data; a storage apparatus 10M for storing the CT image data; a coherent filter processing section 110 for executing a coherent filter processing with respect to the CT image data; and a CBP study processing section 120 for using the CT image data subjected to the coherent filter processing to execute a CBP study processing.

The coherent filter processing section 110 includes a dispersed value estimation section 111, weight function calculation section 112, and pixel value calculation section (coherent filter section) 113. Functions of these dispersed value estimation section 111, weight function calculation section 112, and pixel value calculation section 113 will be described hereinafter in detailed description of a coherent filter processing.

The CBP study processing section 120 includes an ROI setting support section 121, time-density curve preparation section 122, cerebral artery time-density curve correction section 123, MTF processing section 124, index calculation section 125, map preparation section 126, and map synthesis section 127.

The ROI setting support section 121 prepares and provides information (AT, PT, and TT maps for a cerebral artery ROI) for supporting an operation to set a region of interest ROI with respect to cerebral artery and vein on an CT image.

Furthermore, the cerebral artery ROI is separately set in regions of left and right brain, for example, with respect to an anterior cerebral artery (ACA), medial cerebral artery (MCA), and posterior cerebral artery (PCA) as objects. Therefore, in this example, three for each side, that is, six cerebral artery ROI in total are set. Moreover, in order to correct a time-density curve Ca(t) of the cerebral artery, another time-density curve Csss(t) is used. This time-density curve Csss(t) is prepared with respect to the ROI set on a sufficiently thick vessel in which a pixel not including a partial volume exists. ROI of Csss(t) is set, for example, in a thickest upper sagittal sinus venosus in cerebral vessels.

The time-density curve preparation section 122 prepares the time-density curve concerning the cerebral artery, cerebral vein, and cerebral tissue (capillary) from dynamic CT image data (a plurality of image data continuous with time) stored in the storage apparatus 10M. Moreover, the time-density curve Ca(t) of the cerebral artery is separately prepared, for example, for each of six set cerebral artery ROIs. The time-density curve Csss(t) of the cerebral vein is prepared with respect to the cerebral vein ROI set in the upper sagittal sinus venosus. Moreover, the time-density curve Ci(t) for the cerebral tissue is prepared for each of all pixels on the cerebral tissue as objects.

In order to remove influences of noise and partial volume effect, the cerebral artery time-density curve correction section 123 corrects the time-density curve Ca(t) of the cerebral artery based on the time-density curve Csss(t) of the upper sagittal sinus venosus. The correction method will be described later. The MTF processing section 124 calculates a modulation transfer function MTF for each of all the pixels in a cerebral tissue region as objects based on the corrected time-density curve Ca(t) of the cerebral artery and time-density curve Ci(t) for the cerebral tissue by a box-MTF method.

An index calculation section 125 calculates indices (CBP, CBV, MTT, Err) indicating blood flow circulations from the calculated modulation transfer function MTF for each of all the pixels in the cerebral tissue region as the objects. THE map preparation section 126 generates the maps of the calculated indices for each cerebral artery (ACA, MCA, PCA). The maps are prepared by types of indices (=4)×the number cerebral arteries (three including ACA, MCA, PCA)=12 types with respect to each slice. In multi-slice, slice-number times the types of maps are prepared. The map synthesis section 127 is disposed in order to reduce the enormous number of maps by synthesis processing and enhance diagnosis efficiency.

A coherent filter processing and CBP study processing will be described hereinafter in order.

A principle of the coherent filter will briefly be described. For example, 3×3 local pixels in the vicinity are weighted-averaged, and this weighted average value is used as the value of a local center pixel. Weights of peripheral pixels are changed in accordance with similarity between the center pixel and peripheral pixel. Here, the similarity is an index indicating a degree of possibility that the pixels are anatomically close tissues, concretely, cerebral tissues (capillaries) under control of the same cerebral artery. A high weight is given to a pixel having a high similarity, and conversely a low weight close to zero is given to a pixel having a low similarity, so that noise is suppressed, and drop of the spatial resolution can be inhibited. Moreover, in the following, the similarity can appropriately be replaced with fidelity or risk rate.

In the present embodiment, the brain of the subject into which a contrast medium having no cerebral vascular permeability, for example, an iodinated contrast medium is injected (intravenous injection) is used as a scanning object, and a plurality of continuously acquired CT images (dynamic CT images) are used to calculate the similarity by comparison of the time-density curves of the respective pixels. Therefore, certainty of the similarity depends on and is determined by a sampling frequency, the number of images per unit time, and sampling number, that is, the number of all images. Therefore, it is effective to reduce a scan interval, for example, to 0.5 second.

(Coherent Filter)

(General Description of Coherent Filter)

(Pixel Value v(x))

In general, a digital image acquired via scan means such as a camera and CT scanner is constituted of a plurality of pixels (or the image can be considered as a set of pixel). In the following description, the position of the pixel is represented as a vector x (i.e., the vector of a coordinate value), and the value of the pixel x (i.e., a numeric value indicating shading, CT number HU) is represented as a K-dimensional vector. With the two-dimensional image, the pixel x is a two-dimensional vector indicating a coordinate value (x,y) indicative of a position on the image. A "pixel value v(x)" defined with respect to a certain pixel x is represented as follows.

$$v(x)=(v_1(x),v_2(x),\ldots,v_K(x)) \quad (1)$$

wherein $v_1(x)$, $v_2(x)$, . . . , $v_K(x)$ in the right side of the equation (1) will hereinafter be referred to as "scalar values" with respect to the pixel x.

For example, when the image is a "color image", each pixel has brightness (scalar value) of three primary colors (red, green, blue), and therefore pixel value v(x) of each pixel can be considered as a K=3 dimensional vector. That is, suffixes of the right side of the equation (1) are associated, for example, with "red", "green", and "blue". Moreover, for example, when the image is a dynamic image constituted of K still images, and the pixel of the n-th image has a scalar value $v_n(x)$, the pixel values (scalar values) possessed by the pixels x of the same common point (same coordinate) are arranged on K still images to constitute a K-dimensional vector value $v_n(x)=(v_1(x), v_2(x), \ldots v_K(x))$, and this value is a pixel value as a vector value described hereinafter.

(Similarity (Fidelity or Risk Rate) and Weight)

A set N(x) of appropriate peripheral pixels is considered with respect to the pixel x (this set N(x) may include the pixel x). Subsequently, a weight w(p(x,y)) of a peripheral pixel y as an element of N(x) with respect to a center pixel x is considered. This weight w(p(x,y)) has the following properties.

(Similarity p(x,y))

First, the meaning of a function p(x,y) which influences the value of the weight w(p(x,y)) will be described. This p(x,y) is means for quantifying the "similarity" mentioned in the present embodiment. In general, this value indicates a concrete numeric value indicative of a degree of similarity between the center pixel x and peripheral pixel y∈N(x) in some meaning (e.g., a degree of a statistical difference recognized between the pixel values v(x) and v(y) of both pixels x and y).

More concretely, for example, with p(x,y) indicating a large value, a possibility that the pixels x and y have "no statistically significant difference (i.e., a high similarity)" and are similar to each other is judged to be high. With p(x,y) indicating a small value, the pixels x and y are judged to "have the statistically significant difference (i.e., low similarity)".

Furthermore, the pixel values v(x) and v(y) (or scalar values $v_1(x), \ldots, v_K(x)$ and $v_1(y), \ldots, v_K(y)$) necessarily include noise. For example, considering that the image is acquired by a CCD image pickup device, the noise generated by a dark current in the device and irregular fluctuation of light amount incident from an outer world exist in the respective pixels constituting the image.

The noise generally have various values with respect to all the pixels. Therefore, even if the pixels x and y reflect the same object (in the outer world), the pixels do not have the same value on an actually observed image in some case. Conversely, if situations having the respective noise removed are assumed in the pixels x and y reflecting the same object, these are displayed (=recognized as such) on the image as representations of the same object, or both essentially have the same (or very close) pixel value.

Then, the above-described properties of the noise are considered, and a concept of "null hypothesis" well known in a statistical inspection method is used. Then, this p(x,y) can concretely be the as follows. That is, a null hypothesis H "the pixels x and y have the same pixel value, when the respective noise are removed", in other words "v(x)=v(y), where a difference resulting from the noise of both the pixels is removed" (i.e., when this proposition is established, "the similarity between the pixels x and y is supposed to be high (fidelity is large") is assumed. Then, the function p(x,y) can be constituted as the risk rate (or a significant level), when the hypothesis H is rejected (in this case, p(x,y) is defined as a function such that a value range is [0, 1] (p(x,y)∈[0, 1])).

Therefore, when the risk rate p(x,y) is large, that is, the rejection is inaccurate with a high risk rate, a possibility of satisfaction of the hypothesis H is high. However, conversely, when the rate is small, that is, the rejection is inaccurate with a low risk rate, a possibility of not satisfying the hypothesis H can be the to be high (it is to be noted that, as a well known matter in the statistical verification, even with the hypothesis H not "rejected", this does not mean that the hypothesis is "true". In this case, this only means that the proposition indicated by the hypothesis H cannot be denied).

(Weight w(p(x,y)))

As apparent from a way of representation, the weight w(p(x,y)), the weight w(p(x,y)) is a function of the risk rate p(x,y) as described above. In more general, the weight is a function of fidelity. Assuming that the fidelity is p(x,y), the function can be constituted to be w(ρ(x,y)). Moreover, generally speaking, a weight function w acting on the risk rate p(x,y) obtained with respect to combinations of x and y in order to obtain the weight w(p(x,y)) has an action of realizing the "rejection". Concretely, when the risk rate p(x,y) is large, the weight function w, i.e., the weight w(p(x,y)) indicates a large positive value. In the opposite case, the function is adjusted to have a small positive value (or "0"). A concretely form of the weight function w will be described later. That is, when the pixels x and y satisfy the proposition indicated by the hypothesis H, the weight w(p(x,y)) indicates a large value. In the opposite case, the weight has a small value. As one example, particularly w may be constituted to indicate two values; "0"; and a constant value other than "0".

Furthermore, a relation among the above-described hypothesis H, risk rate p(x,y), and weight w(p(x,y)) will be summarized. When the null hypothesis H has a high possibility of being correct, a similarity p also increases, and a weight w given to the pixel is raised. On the other hand, the possibility that the null hypothesis H is correct is low, then the similarity p is low, and the weight w given to the pixel is lowered. When contribution (weight) of the weighted average value is changed in accordance with the similarity in this manner, it is possible to inhibit the drop of the resolution and effectively suppress the noise. Moreover, in more general, a weight function w(t) can be the to be a "positive/negative monotonous increase function defined by t∈[0, 1]", and the w(t) may satisfy at least the above-described properties.

(Coherent Filter Processing)

By the above description, a "coherent filter" is derived as follows. That is, first the above-described weights w(p(x,y)) of all pixels y as elements of a set N(x) are calculated with respect to a certain pixel x constituting the image. Subsequently, these weights w(p(x,y)) are used to calculate a new scalar value $v'_k(x)$ constituting the pixel x in the following equation (2).

$$v'_k(x) = \frac{\sum_{y \in N(x)} v_k(y)w(p(x, y))}{\sum_{y \in N(x)} w(p(x, y))} \quad (2)$$

wherein k=1, 2, ..., K. Subsequently $v'_k(x)$ obtained by this equation is used to constitute a converted pixel value (new pixel value) v'(x) of the pixel x as follows.

$$v'(x) = (v'_1(x), v'_2(x), \ldots, v'_K(x)) \quad (3)$$

Here, a filter for converting pixel value $v(y) = (v_1(y), v_2(y), \ldots, v_K(y))$ (including a case of y=x) to $v'(x) = (v'_1(x), v'_2(x), \ldots, v'_K(x))$ is the form of the "coherent filter". As apparent from the equation, this indicates the weighted average value of the scalar value $v_k(y)$ constituting the pixel value.

This processing brings about the following result. That is, this indicates a vector constituted of the weighted average value $v'_k(x)$ having a raised contribution of the pixel y which seems to surely have the same pixel value as the pixel value v'(x) of the pixel x with the noise removed therefrom (=which has a high possibility of satisfying the preposition of the hypothesis H). Moreover, if a sufficient number of pixels y exist, the pixel value v'(x) has a value not lowering the resolution without deviating from a true value essentially possessed by the pixel x and while suppressing the noise by an action of the above-described averaging.

Furthermore, even when the risk rate p(x,y) is small, therefore the null hypothesis H is "rejected", and the weight w(p(x,y)) is reduced, as seen from the above description, the hypothesis is not necessarily completely "rejected". This depends on the concrete form of the weight function w described later, but even when the risk rate p(x,y) is close to "0" (=0%), w(p(x,y))≠0 may be set. However, the weight has a much smaller positive value as compared with p(x,y) close to "1". It is to be noted that p(x,y)=1 corresponds to v(x)=v(y) as described later.

That is, instead of completely rejecting the hypothesis, a small contribution may be recognized. It is to be noted that, in this case, w(p(x,y))=0 has the same meaning as that of the compete rejection.

This processing can generally be the as follows. That is, when a plurality of pixels x constituting a certain image exist, fidelity p(x,y) of this pixel x with a certain arbitrary pixel y (y∈N(x) was set in the above description) is quantized. When h above description) is quantized. When the fidelity is large, a large contribution of the pixel y is recognized in a weighted averaging processing using the pixel value v(y). When the fidelity is small, only the small contribution is recognized. Thereby, it can be the that the noise of the pixel x is effectively suppressed in an image processing method. When the pixels x and y are so-called "similar to each other", the pixel y is allowed to further contribute to the averaging processing. In other words, when the pixels are "not similar to each other", the pixel y is totally or almost ignored (the weight is set to zero or an approximate value).

When the whole image is subjected to this processing, blur of the image, that is, the drop of the spatial resolution hardly occurs, and a remarkably high noise suppressing effect can be fulfilled. Moreover, the use is not limited to noise suppression. For example, even in a field of pattern recognition, the weight function, or the coherent filter is set in a preferable concrete form. Then, a superior effect can be fulfilled.

Here, the above-described "dynamic CT" scan is a scan system in which the X-ray tube 101 and X-ray detector 102 repeatedly photograph the same portion of the subject P (the repeated scan is often performed by continuous rotation in a repeated scan, and continuous rotary CT apparatus) to successively acquire projection data, a reconstitution processing is successively performed based on the projection data, and a time series of images are obtained. In this case, the image display in the image display section 107 is controlled, for example, by a counter (not shown), so that the display is performed a constant time after the scan start or end point for collecting the projection data as an original image.

Therefore, the image acquired/displayed in this manner is a so-called dynamic image including the time series of a plurality of still images similarly as in the movies. It is to be noted that such scan system is typically used to inject the contrast medium into the subject P, observe/analyze a change with an elapse of time, and analyze a pathological state of an affected area such as stenosis and occlusion in the vessel. Moreover, even a system of performing the CT scan of the same portion only twice before and after contrast medium administration can be considered as a broad dynamic CT scan.

Furthermore, in a conventional art, during the above-described "dynamic CT" scan, for example, when the subject P has some change during K scan operations (e.g., a concentration change of the contrast medium, or a respiratory operation is generally considered), the smoothing has to be performed in a time direction in order to suppress the image noise without impairing the spatial resolution. As a result, a problem that the time resolution is impaired cannot be avoided.

However, the image acquired by the dynamic CT scan is a dynamic image as described above, and scanned for a purpose of observing the change with time in detail. Therefore, the impairment of the time resolution cannot essentially be the to be a preferable situation.

With the use of the coherent filter, the following dynamic coherent filter processing can be carried out in which the time resolution is not impaired and the noise can be suppressed from all of K still images (a plurality of images).

First, for the pixel x defined with respect to K still images as the dynamic images obtained as described above, the following can be constituted as the pixel value v(x) as described above.

$$v(x) = (v_1(x), v_2(x), \ldots, v_K(x)) \quad (1)$$

Here, suffixes 1, 2, ..., K in right-side terms are serial numerals of K still images.

Next the concrete form of a weight function w1 in this case is represented, for example, by the following equation (4).

$$w1(p(x, y)) = \exp\left[-\left\{\sqrt{\sum_{k=1}^{k} \frac{\{v_k(x) - v_k(y)\}^2}{K(2\sigma_k)^2}}\right\}^c\right] \quad (4)$$

wherein y∈N(x), and this set N(x) may arbitrarily be set with respect to the pixel x (=may also be set by any standard). However, in actual, a possibility of satisfying the hypothesis "v(x)=v(y), where a difference resulting from the noise of both pixels is removed" by the pixel x and the pixel y disposed apart from the pixel x can be the to be generally low. Therefore, to limit the set N(x) on an assumption that the set N(x) is a set of pixels disposed in the vicinity of the pixel x has a practical significances such as improvement of a calculation speed.

Therefore, here, as one example, the set N(x) is assumed to be a set of pixels included in a rectangular peripheral area centering on the pixel x. More concretely, for example, for the set N(x) when 128×128 pixels in total constitute one noted still image, an area for 3×3 pixels centering on the pixel x is defined. Furthermore, when 512×512 pixels constitute the still image, an area for 13×13 pixels centering on the pixel x may be defined.

Moreover, $\sigma_k$ in the above equation (4) is a standard deviation of the noise estimated on an assumption that each of k still images has a constant common degree of noise. On the other hand, C is an adjustable parameter which determines a degree of action with the weight wl(p(x,y)) assigned to the above equation (4). These $\sigma_k$ and C will be described hereinafter in order.

First, $\sigma_k$ in the equation (4) will be described (hereinafter described as a dispersal $\sigma_k^2$). As described above, this $\sigma_k^2$ is a dispersal of noise component possessed by the scalar value of each pixel on k still images. Moreover, the dispersal $\sigma_k^2$ in the above equation (4) is estimated on an assumption that the scalar value of each pixel of k images includes noise with a constant value of dispersal $\sigma_k^2$. In general, this assumption has a sufficient validity in the following background.

When the size of the subject P and the structures of the X-ray tube 101, X-ray detector 102, and reconstitution section 106 are constant, and an energy of X ray radiation is set to be constant, the noise of the CT image is determined by an X ray radiation dose, that is, a product of a tube current of the X-ray tube 101 in a proportional relation and an irradiation time (so-called current time product (mA·s)).

On the other hand, it is also known that the noise of CT image is additive and substantially follows Gaussian distribution. That is, assuming that the true value (value with the contribution of the noise removed therefrom) is $v_n^0(x)$ with respect to an arbitrary scalar value $v_n(x)$ (n=1, 2, ..., K) constituting the pixel value v(x) of a certain pixel x, a value of difference $v_n(x) - v_n^0(x)$ substantially follow Gaussian distribution with a mean of 0 and dispersal $\sigma_k^2$. It is to be noted that the X ray radiation dose or current time product mAs is substantially in inverse proportion to the dispersal $\sigma_k^2$ of the noise.

Moreover, the dispersal $\sigma_k^2$ depends on the position of the pixel x (e.g., each coordinate value x=(x,y) as described above). In a usual X-ray CT scanner 100, a physical X-ray filter for adjusting the X ray radiation dose (e.g., called a "wedge" or "X-ray filter" formed of a copper foil or solid metal blank) is disposed between the X-ray tube 101 and X-ray detector 102. The dispersal is therefore negligible. The wedge has a function of using a fact that the subject P is formed of a material substantially with the same density as that of water, and attenuating a part of the X ray radiation dose so that the same degree of X ray radiation dose is detected in any X-ray detector 102. Therefore, according to the wedge, as a result, an effect is produced that the dispersal $\sigma_k^2$ of the noise has a substantially constant value regardless of the position of the pixel x. In general, the wedge is disposed for an essential purpose of effectively using the dynamic range of the X-ray detector 102.

As described above, it is proper to estimate that the dispersal $\sigma_k^2$ is substantially constant with respect to all pixels on k still images in K still images acquired by the dynamic CT scan. Of course, it can easily be considered that the present embodiment is extended for the dispersal different with each pixel.

Furthermore, to concretely calculate the above equation (4), a numeric value assigned to the dispersal $\sigma_k^2$ is a problem. This is because the form of the distribution of the noise can usually be assumed (Gaussian distribution in the above), but the concrete value of the dispersal $\sigma_k^2$ is unclear in many cases.

Furthermore, in general, the radiation dose (X-ray tube current×radiation time (mAs)) may be changed every scan. When the scan is performed in this manner, the dispersal $\sigma_k^2$ differs with each image in this case.

In addition, assuming that the dispersal of the noise of the scalar value of each pixel is $\sigma_k^2$ in the k-th image (k=1, 2, ..., K) and the radiation dose for use in the scan of the k-th image is $R_k$, $\sigma_k^2$ is proportional to $R_k$. Therefore, when $\sigma_{k_0}^2$ can be designated with respect to at least one $k=k_0$, $\sigma_k^2$ can accurately be estimated also with respect to another k by the following.

$$\sigma_k^2 = \sigma k_0^2 \frac{R_k}{R_{k0}} \tag{5}$$

In the present embodiment, the concrete numeric value of $\sigma_k^2$ can be estimated with respect to at least one k by the following method.

A method of using N ($1 < N \leq K$) images which can be assumed to hardly have a change in the subject P in K scan operations and obtaining an anticipated value $E[\sigma_k^2]$ with respect to the dispersal $\sigma_k^2$ by actual measurement is effective. To simplify the following description, the radiation dose in N images is the same. Therefore, it is assumed that $\sigma_k^2$ is constant (written as $\sigma^2$) with respect to k=1, 2, ..., N. The noise included in the respective scalar values $v_1(x_f)$, $v_2(x_f)$, ..., $v_K(x_f)$ constituting the pixel value $v(x_f)$ of a certain pixel $x_f$ in these N images are expected to follow Gaussian distribution with the mean of 0 and dispersal of $\sigma^2$ as described above. The mean value is obtained using the following equation (6).

$$v^*(x_f) = \frac{1}{N} \sum_{k=1}^{N} v_k(x_f) \tag{6}$$

Then, an anticipated value $E[\sigma^2]$ can be obtained with respect to the true dispersal $\sigma^2$ as follows.

$$E[\sigma^2] = \frac{1}{N-1} \sum_{k=1}^{N} \{v_k(x_f) - v*(x_f)\}^2 \tag{7}$$

Moreover, it can be considered that the anticipated value $E[\sigma^2]$ of the dispersal is proper with respect to all the pixels x on all the K still images as described above. A likelihood of the anticipated value is guaranteed for use as a substitute for the true dispersal $\sigma^2$ by not less than a constant degree. Therefore, in the actual calculation of the above equation (4), this $E[\sigma^2]$ may be assigned to $\sigma^2$ of the equation (4).

Furthermore, this $E[\sigma^2]$ may more concretely be obtained by actual measurement, for example, based on the first and second still images in K still images, and this corresponds to an assumption of N=1 in the above equations (6) and (7). Moreover, for the pixel $x_f$ for use in the actual calculation of the above equations (6) and (7), for example, only an appropriate pixel $x_f$ may be designed to be selected excluding a portion in which air and bone are scanned. When a plurality of pixels are selected, all the obtained values of $E[\sigma^2]$ are averaged. Furthermore, in general, an influence by movement of the subject P may also be designed to be preferably suppressed.

Even with the inconstant radiation dose in the scan of these N images, it can easily be inferred that the proportionality of $\sigma_k^2$ to $R_k$ is used to correctly estimate $\sigma_k^2$.

Subsequently, parameter C in the above equation (4) will be described. First, in the equation (4), an idea of risk rate p(x,y) described above in the general mode is included as follows. That is, the inside of a root sign in a right side numerator of the equation (4) agrees with $\chi^2$ value assumed to follow a so-called $\chi$ square distribution, and is divided by $(2\sigma)^2$. Whole parentheses are placed on the shoulder of e, and this value is the risk rate p1(x,y). That is, the following equation is results.

$$p1(x, y) = A \exp\left\{-\sum_{k=1}^{K} \frac{\{v_k(x) - v_k(y)\}^2}{K(2\sigma_k)^2}\right\} \quad (8)$$

Moreover, the above equation (4) is converted to the following with respect to p1(x,y) represented in the equation (8).

$$w1(p(x, y)) = \{p1(x, y)\}^{-\frac{C}{2}} \quad (9)$$

wherein A is a constant standardized so that p1 indicates a value of (0 to 1).

Eventually, in the equation (4), the risk rate p(x,y) described above in the general mode is not positively displayed, but the mode of the weight w1(p(x,y)) can certainly be regarded as the function of the risk rate (=p1(x,y)) (equation (9)) as described above, that is, the mode is a "function of fidelity". As described above, the risk rate and fidelity are in such a relation that with an increase of one of them, the other also increases.

Furthermore, as seen from the above equation (9), the parameter C effectively determines a degree of sensitive reaction of the weight w1(p(x,y)) to the risk rate p1(x,y). That is, when C is increased, p1(x,y) slightly decreases, and w1(p(x,y)) approaches 0. Furthermore, when C is reduced, such sensitive reaction can be suppressed. Moreover, C may concretely be set to about 1 to 10, and preferably C=3 may be set.

In the present embodiment, the similarity between the center pixel x and peripheral pixel y is judged. In other words, the rejection of the above-described null hypothesis H concerning both pixels x and y is determined based on the risk rate p1(x,y) by a so-called X square inspection method (statistical inspection method) as apparent from the above.

Moreover, as seen from the above equation (4), in the present invention, a procedure of calculating the risk rate p(x,y) with respect to the respective combinations of x, y and subsequently obtaining the weight w(p(x,y)) does not necessarily have to be executed. Without concretely obtaining the risk rate p(x,y), synthesis function (w°p) may directly be calculated in a constitution.

As described above, when the dispersal $\sigma^2$ is estimated (e.g., $E[\sigma^2]$ of the equation (7)), and the parameter C is appropriately determined (e.g., C=3), the equation (4) can be used to obtain the concrete weight w1(p(x,y)) with respect to all the pixels y included in the set N(x) (e.g., the above-described area for 3×3 pixels centering on the pixel x) defined with respect to the certain pixel x. Subsequently, instead of w(p(x,y)) in the equation (2), this w1(p(x,y)) can be used to perform the concrete numeric value calculation of the coherent filter. Moreover, as a result, without impairing of course the time resolution and also the spatial resolution, the pixel value with the strongly suppressed noise v'(x)=(v'$_1$(x), v'$_2$(x), . . . , v'$_K$(x)) (=equation (3)), that is, the K still or dynamic images with the strongly suppressed noise can be obtained.

This image processing is schematically shown for ease of understanding in FIGS. 3A to 3C. That is, first in FIG. 3A, in 1, 2, . . . , K still images, with respect to the certain pixel x, a rectangular area $N^{3\times3}(x)$ for 3×3 pixels centering on the pixel x is assumed. Assuming that the pixel in the left corner of the rectangular area $N^{3\times3}(x)$ is $y_1$, the pixel $y_1$ has a pixel value $v(y_1)$.

Moreover, by scalar values $v_1(y_1), v_2(y_2), \ldots, V_K(y_1)$ constituting the pixel value $v(y_1)$ and the scalar values $v_1(x)$, $v_2(x), \ldots, v_K(x)$ in the pixel value $v(x)$, a weight w1(p(x,$y_1$)) is calculated by the above equation (4) (FIG. 3B). Furthermore, with respect to the remaining pixels $y_2, \ldots y_8$ of the rectangular area $N^{3\times3}(x)$, eventually as shown in FIG. 3B, w1(p(x,$y_1$)), . . . , w1(p(x,$y_8$)), and w1(p(x,x)) can similarly be obtained. In this case, from the equation (8), the risk rate p(x,y) is "1", and therefore the weight w1(p(x,y)) is also "1" from the equation (9) (=a maximum weight is applied).

Subsequently, the weights w1(p(x,$y_1$)), . . . , w1(p(x,$y_8$)), w1(p(x,x)) obtained in this manner are multiplied by the scalar values $v_k(y_1), v_k(y_2), \ldots, v_k(y_8), v_k(x)$ of the corresponding pixel in the k-th image to obtain a total sum (corresponding to the numerator in the above equation (2)). The sum is divided by the sum (similarly corresponding to the denominator of the equation (2)) of the weight w1 concerning the rectangular area $N^{3\times3}(x)$. Then, with respect to the pixel x in the k-th image, the scalar value v'$_k$(x) with the suppressed noise can be obtained (FIG. 3C). Moreover, with respect to all the images k=1, 2, . . . , K, the same weights w1(p(x,$y_1$)), . . . , w1(p(x,$y_8$)), w1(p(x,x)) are used to obtain the scalar value v'$_k$(x) with the suppressed noise, and thereby the pixel value with the suppressed noise in the pixel x v'$_k$(x)=(v'$_1$(x), v'$_2$(x), . . . , v'$_k$(x)) is obtained. When the above calculation is repeated with respect to all the pixels x, the K images with the suppressed noise are obtained.

In the image constituted of the pixel value v'(x) calculated with the coherent filter, random noise seen in the original image are sufficiently suppressed.

Figure 4A:
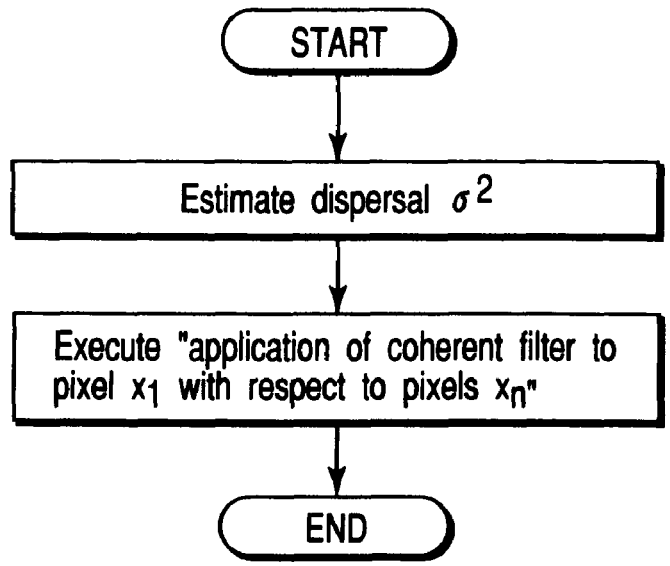
FIGS. 4A, 4B are flowcharts showing a flow of noise suppressing processing by the coherent filter in the present embodiment.
Figure 4B:
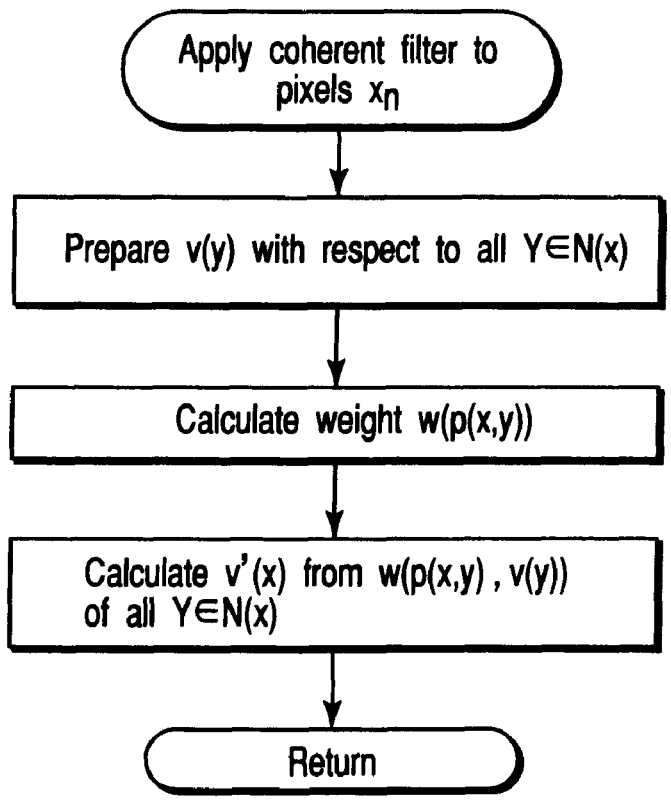

Moreover, the above-described steps may be executed, for example, with reference to flowcharts as shown in FIGS. 4A, 4B. Moreover, to realize the calculation and image display of the respective steps on the actual X-ray CT scanner 100, for example, as shown in FIG. 2, the image processing section 110 including the dispersed value estimation section 111, weight calculation section 112, and pixel value calculation section 113 may be disposed to execute the steps.

In this case, the weight calculation section 112 is configured to obtain the weight w1(p(x,y)) directly from the pixel values v(x) and v(y) as described above. Therefore, the calculation section 112 is an apparatus for directly obtaining the weight without concretely obtaining the value of the risk rate p1(x,y). Moreover, instead of the above-described constitution, a constitution may execute two steps of procedure by a risk rate calculation section (fidelity quantization section) for concretely obtaining the value of the risk rate p1(x,y), and a weight calculation section for obtaining the weight w1(p(x,y)) based on an output of the risk rate calculation section. In any case, the weight calculation section 112 uses the dispersal $\sigma^2$ estimated by the dispersed value estimation section 111, v(x), and v(y) to calculate the weight w1(p(x,y)).

Moreover, the pixel value calculation section 113 uses the pixel values v(x) and v(y), and the weight w1(p(x,y)) whose numeric value is calculated by the weight calculation section 112 to calculate the pixel value v'(x). That is, the calculation section 113 actually executes a step of suppressing the noise of the original image, that is, applies the coherent filter (hereinafter referred to as "the coherent filter is applied").

When the coherent filter is applied to the dynamic image including K still images in the above-described dynamic coherent filter processing, the processing in the image processing section 110 may include: once reconstituting all the still images; subsequently storing the images in the storage apparatus 10M; and applying the coherent filter to the images as a post processing. However, the present invention is not limited to this mode. In the above-described flow of continuous scan, continuous projection data collection, continuous reconstitution, and continuous display, the step of applying the coherent filter may be carried out in real time (hereinafter referred to as "real time coherent filter processing").

In a preferred embodiment of the real time coherent filter processing, every time a new image is scanned and reconstituted, the following processing is performed. Among the first obtained image (image number 1) to the latest image (image number M), the pixel value (scalar value) of the pixel x of the common same point (same coordinate) is arranged on K still images having image numbers M, M−1, . . . , M−K+1 to constitute K-dimensional vector value $v(x)=(v_M(x), v_{M-1}(x), \ldots, v_{M-K+1}(x))$. In this manner, the coherent filter can be applied in the same manner as the above-described "dynamic coherent filter processing". In actual, the pixel value calculation section 113 calculates only the scalar value $v_M'(x)$ corresponding to the latest image (image number M) instead of calculating all elements of the pixel value v'(x). As a result, since a calculation speed is improved, the latest image with the suppressed noise can be displayed in real time.

As another preferred embodiment of the "real time coherent filter processing", a constitution may include: applying the coherent filter in the same manner as described above to obtain $v_1'(x), \ldots, v_K'(x)$ at a time at which K images are first obtained; subsequently using K still images having image numbers M, M−1, . . . , M−K+1 to constitute the K-dimensional vector value by $v(x)=(v_M(x), v_{M-1}'(x), \ldots, v_{M-K+1}'(x))$; and applying the above-described real time coherent filter processing with respect to the value. Additionally, during the real time coherent filter processing, the dimension K of the pixel value vector v(x) can be changed as needed by manual or automatic setting, and this constitution is convenient.

In this manner, by the coherent filter, the CT image in which only the noise is effectively suppressed without deteriorating the space or time resolution is used to carry out the CBP study, the local blood flow circulations in the tissue, that is, the circulations of the blood flow passed through the capillary in the local tissue is quantitatively analyzed, and the indices (CBP, CBV, MTT, Err) indicating the local blood flow circulations are obtained, so that the enhancement of the precision and reliability can be anticipated.

As described above, the CBP study processing is carried out with respect to the image in which the resolution is inhibited from dropping and the noise is removed.

(CBP Study)

As described above, the CBP study includes: obtaining indices of CBP, CBV, MTT, and Err quantitatively indicating the circulations of "the blood flow passed through the capillary" in the cerebral tissue; and outputting a map indicating a spatial distribution of these indices:

CBP: blood flow rate [ml/100 ml/min] per unit volume and time in the capillary for the cerebral tissue;

CBV: blood amount [ml/100 ml] per unit volume in the cerebral tissue;

MTT: blood mean transit time [second] of the capillary; and

Err: index of a deviation residual errors error of an actually measured value from an analysis model.

Furthermore, when the residual errors error Err is low, a high possibility of depending on a reference cerebral artery is meant. Conversely, when the residual errors error Err is high, a low possibility of depending on the reference cerebral artery is meant.

In the CBP study, a contrast medium having no cerebral vessel permeability, such as an iodinated contrast medium, is used as a tracer. The iodinated contrast medium rapidly injected via a cubital vein by an injector flows into a cerebral artery via heart and lung. Moreover, the medium flows out to the cerebral vein from the cerebral artery via the capillary in the cerebral tissue. In this case, the contrast medium having no cerebral vessel permeability, such as the iodinated contrast medium passes through the capillary in a normal cerebral tissue without any extravascular leakage.

The state of passage of the contrast medium is continuously scanned by a dynamic CT, and a time-density curve Ca(t) of the pixel on the cerebral artery, time-density curve Ci(t) of the pixel on the cerebral tissue including the capillary, and time-density curve Csss(t) of the pixel on the cerebral vein are measured from a continuous image.

In the CBP study, an ideal relation established between the time curve Ca(t) of a blood concentration of the cerebral vessel in the vicinity for the cerebral tissue and the time curve Ci(t) of the blood concentration of the capillary with respect to the blood concentration of the contrast medium is used as an analysis model. That is, assuming if the contrast medium is injected via the vessel immediately before the cerebral tissue, the time-density curve in the unit volume (one pixel) for the cerebral tissue including the capillary rises vertically, stays at a constant value, and falls with a slight gradient. This can be approximated with a rectangular function (box-modulation transfer function method: box-MTF method).

The time-density curve Ca(t) of the cerebral artery blood is used as an input function, the time-density curve Ci(t) for the cerebral tissue is used as an output function, and characteristics of a process of passage through the capillary can be obtained as a modulation transfer function represented by the rectangular function.

(Concrete Procedure)

Figure 5:
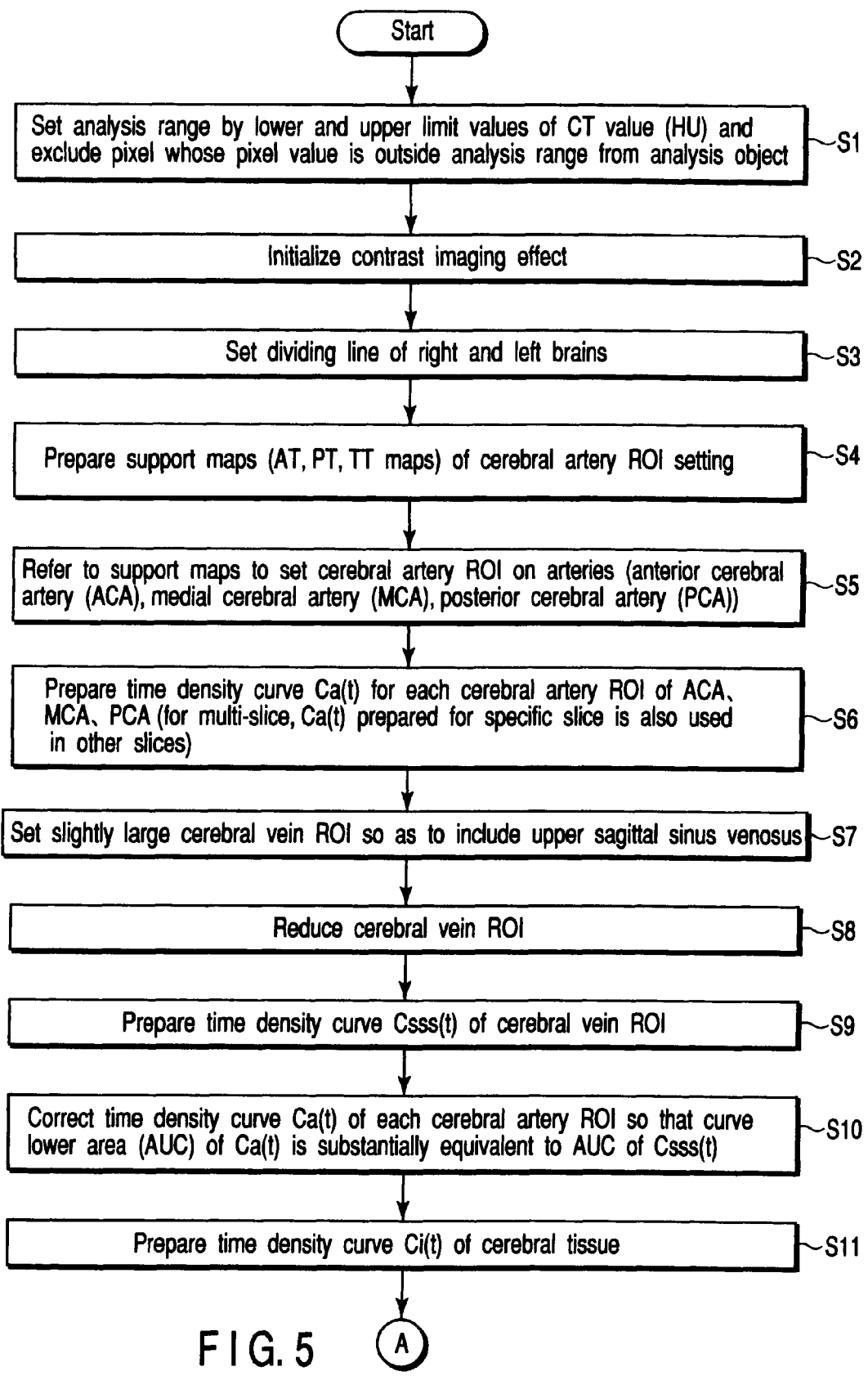
FIG. 5 is a flowchart of a former half of a whole index calculation processing in the present embodiment.
Figure 6:
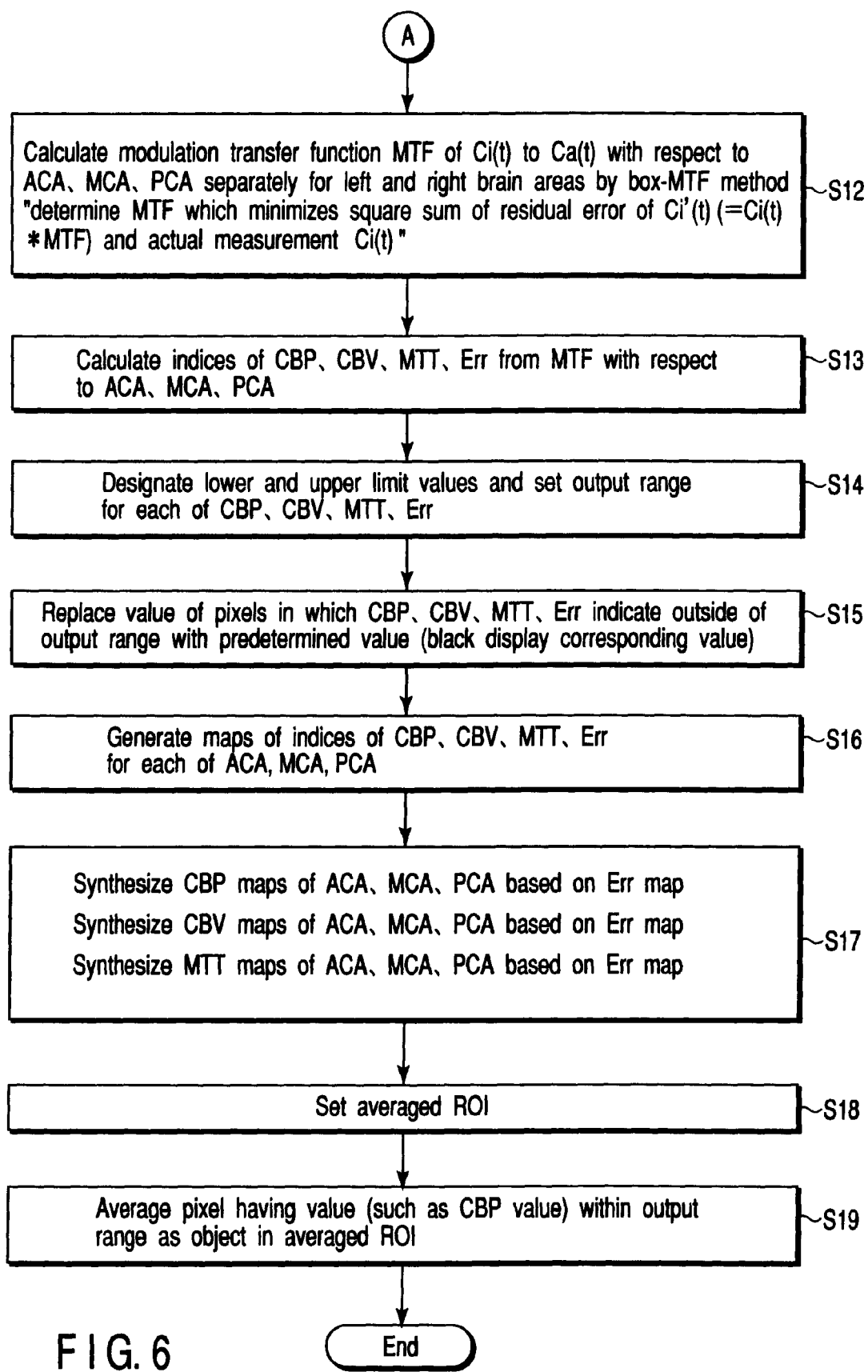
FIG. 6 is a flowchart of a latter half of the whole index calculation processing in the present embodiment.

FIGS. 5 and 6 show a typical procedure of the CBP study according to the present embodiment. First, bolus injection of the vessel such as the cubital vein is performed (the contrast medium is administered at once), and dynamic CT is performed immediately after or before the injection (the same position is repeatedly scanned). As a most typical method, when the bolus injection of the cubital vein is performed, the scan is repeated, for example, at an interval of 0.5 to 2 seconds for about 20 to 40 seconds. A CT number of each pixel (x,y) of a j-th image among N CT images obtained by the dynamic CT is assumed as (x,y,j). This is nothing but a sampled value of a time-density curve (smooth curve) f(t,x,y) in the pixel (x,y).

First, as a preprocessing, in step S1, for the respective CT images, the pixels which are apparently judged to correspond to tissues other than the cerebral tissue are excluded from analysis object. That is, the pixel indicating a value outside a range supposed as the CT number for the cerebral tissue (e.g., a CT number of 10 to 60 HU) is a pixel corresponding to air, bone, or fat, is unrelated with a fixed quantity of the cerebral blood flow, and may be negligible. This analysis range is set to 10 to 60 HU as default, but can arbitrarily be set via the input section 109.

Moreover, as a preprocessing, in step S2, a contrast enhancement effect is initialized. To obtain the contrast enhancement effect in each pixel (rise of CT number), the images (a plurality of images are generally obtained) before the contrast medium reaches the tissue corresponding to each pixel (x,y) are denoted with serial numbers 1, 2, ..., K, and a time mean value is obtained as follows.

$$\left(\sum_{j=1}^{K} v(x, y, j)\right) / K \quad (10)$$

This value is set to b(x,y). Moreover, a pixel value v(x,y,j) of each image j=K+1, K+2, ..., N is calculated as follows.

$$q(x,y,j)=v(x,y,j)-b(x,y)$$

With j<K, the following may be set.

$$q(x,y,j)=0$$

To simplify the processing, the same K may be used with respect to any pixel. Thus obtained q(x,y,j) can be considered to be nothing but a sampled value of a time-density curve q(t,x,y) as a smooth continuous curve in t=t1, t2, ..., tN. This q(t,x,y) is used to perform a quantitative analysis of the cerebral blood flow.

In the quantitative analysis, first, right and left hemispheres can be separated on the CT image. In the above-described CBP study, the state of the blood flow circulation of the capillary is obtained as a modulation transfer function MTF of the time-density curve Ci(t) for the cerebral tissue with respect to the time-density curve Ca(t) of the cerebral artery. Therefore, unless the cerebral tissue as the analysis object depends on the cerebral artery of the referred curve Ca(t), the calculation is useless. Separate cerebral artery time-density curves Ca(t) are used at least for the left and right brain to individually analyze the objects. That is, the time-density curves Ca(t) of the cerebral artery of the left brain is used only in analyzing the cerebral tissue of the same left brain. Similarly, the time-density curves Ca(t) of the cerebral artery of the right brain is used only in analyzing the cerebral tissue of the same right brain. This effectively reduces the useless calculation.

Figure 7:
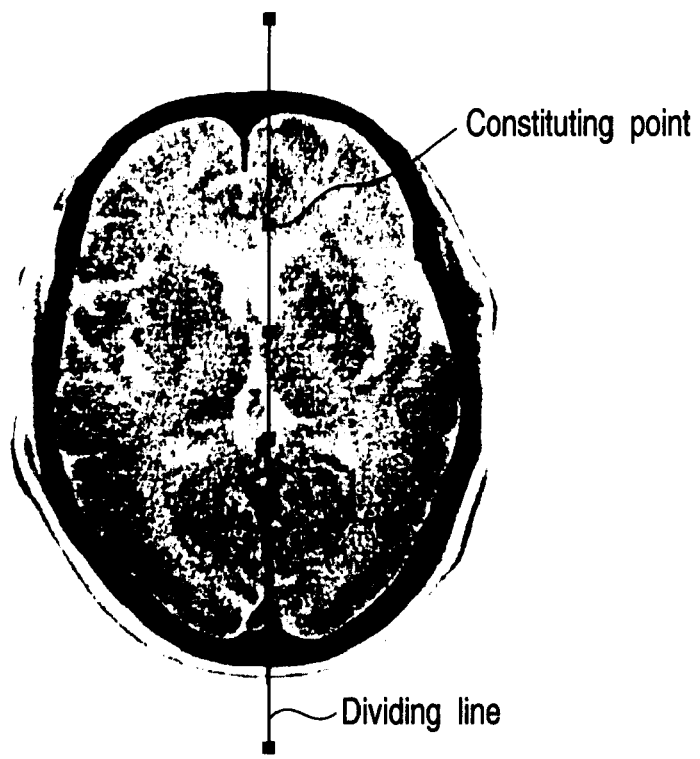
FIG. 7 is a diagram showing one example of a dividing line of step S3 of FIG. 5.

To divide the brain into the left and right hemispheres, as shown in FIG. 7, a dividing line is superimposed and displayed as a graphic upon the CT image in a screen (S3). The dividing line may first be constituted to be displayed in an image middle. An operator refers to the image, moves the dividing line, moves a plurality of points constituting the dividing line, arbitrarily bends the line, and thereby divides the left and right areas.

When the brain is divided into the left and right hemispheres and analysis ranges are confined in the respective areas, the number of analysis processing steps can be reduced. That is, the time-density curves Ca(t) of the cerebral artery of the left brain (left ACA, MCA, PCA) is used only in analyzing the left brain area (modulation transfer function optimization processing). Similarly, the time-density curves Ca(t) of the cerebral artery of the right brain (right ACA, MCA, PCA) is used only in analyzing the cerebral tissue of the same right brain. To reduce the number of analysis processing steps, the left and right hemispheres are further divided into areas, and the analysis processing may be confined in a much narrower area.

To divide the area, a geometric configuration method such as the Voronoy method can be used. As well known, the Voronoy method is a technique for frequent use in a field of optimum arrangement of facilities such as a hospital, shop, and fire station, and is characterized in that a plane is divided into a plurality of areas of influence in accordance with distances from a large number of points (corresponding to the shops, generatrix) disposed on the plane.

Figure 8:
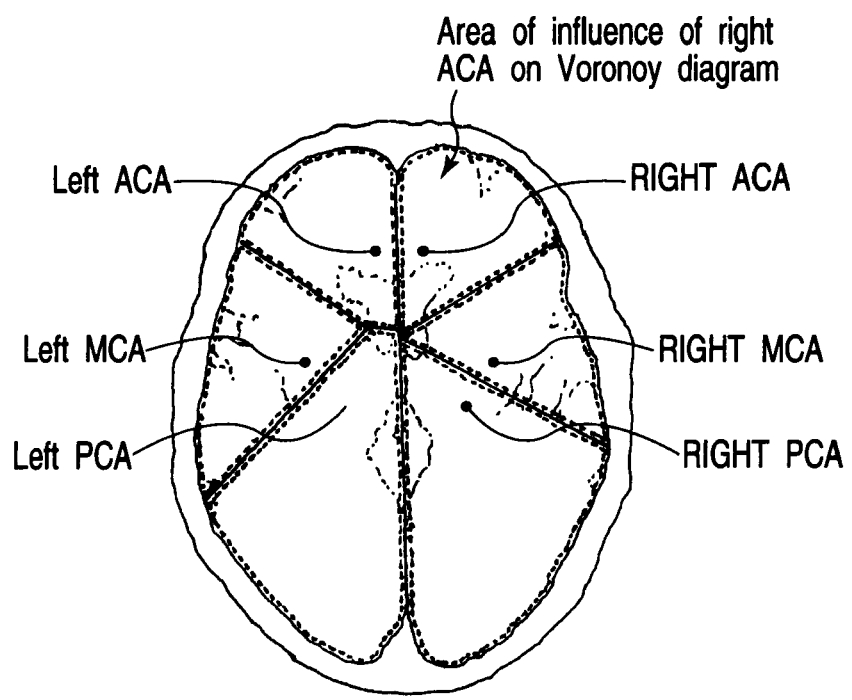
FIG. 8 is a diagram showing an influence range of each cerebral artery on Voronoy diagram for use in decreasing the number of processing steps of step S12 of FIG. 6.

As shown in FIG. 8, in the present embodiment, the Voronoy method is separately applied to the left and right hemispheres. The left ACA, MCA, PCA are used as three generatrices to divide the left brain area into areas of influence of left ACA, MCA, PCA. Voronoy point is set to a center of a circle passed through three generatrices corresponding to the left ACA, MCA, PCA. Centering on Voronoy point, a perpendicular bisector of two generatrices of the left ACA and MCA, perpendicular bisector of two generatrices of the left MCA and PCA, and perpendicular bisector of two generatrices of the left ACA and PCA are connected to one another. The left brain area is divided into three areas of influence by these perpendicular bisectors. Similarly, right ACA, MCA, PCA are used as three generatrices to divide the right brain area into areas of influence of right ACA, MCA, PCA.

The modulation transfer function MTF of the time-density curve Ci(t) for the cerebral tissue to the time-density curve Ca(t) of the left ACA is confined to the area of influence of the left ACA and obtained for each pixel. Similarly, the modulation transfer function MTF is confined to the area of influence with respect to the left MCA and PCA, and right ACA, MCA, PCA, and obtained for each pixel.

When the left and right hemispheres are divided into a plurality of areas of influence, and an analysis range is confined to each area of influence, the number of analysis processing steps can further be reduced.

Figure 9:
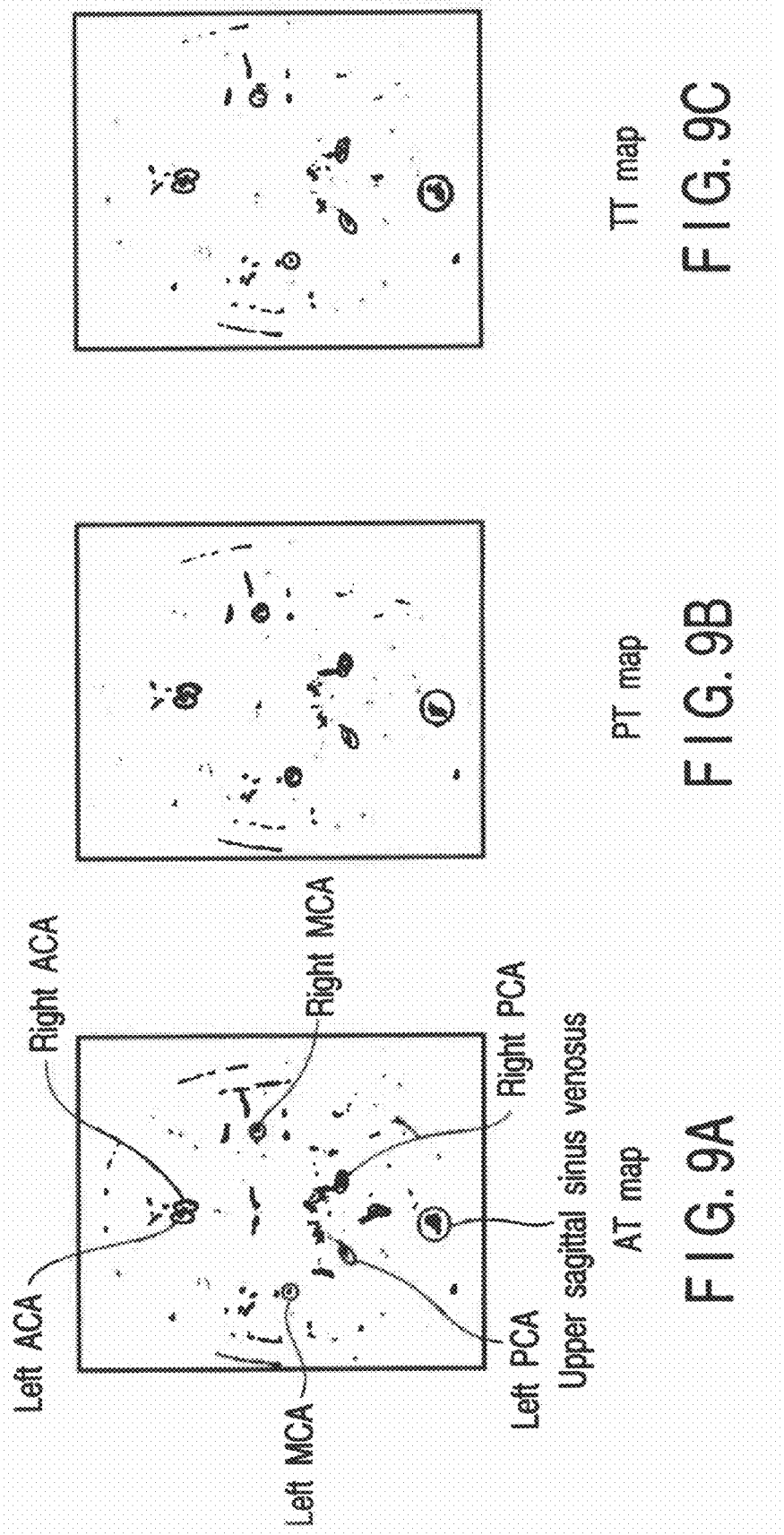
FIGS. 9A, 9B, 9C are diagrams showing AT, PT, and TT maps of step S4 of FIG. 5.
Figure 10:
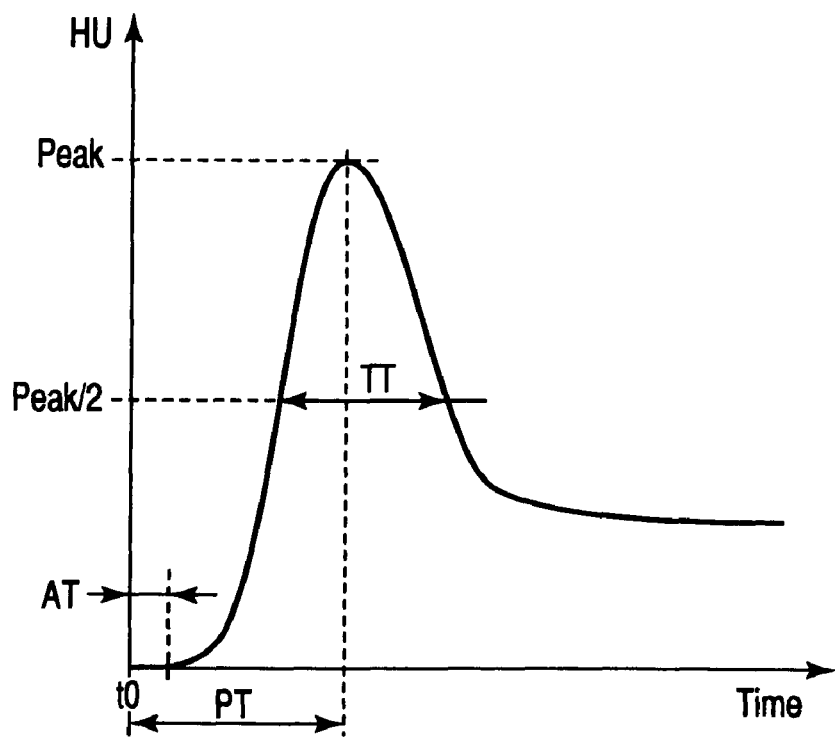
FIG. 10 is a diagram showing AT, PT, TT of the step S4 of FIG. 5.

Subsequently, a cerebral artery ROI is set on the cerebral artery on the CT image. To enhance the precision of the setting and facilitate the setting, the ROI setting support section 121 prepares a support map, and the map is displayed separately from or upon the CT image (S4). As shown in FIGS. 9A to 9C, examples of the support map includes an appearance time (AT) map, peak time (PT) map, and transit time (TT) map. With respect to the respective pixels, as shown in FIG. 10, time AT from an arbitrary time T0 before the contrast imaging (e.g., data collection start time) until a contrast medium concentration reaches several percents (e.g., 1%) of a peak, time (peak time) PT from the time T0 until the contrast medium concentration reaches the peak, or TT indicating a movement time of the contrast medium, for example, with a half value width is calculated, and generated and displayed as the map. In default, all types including these AT, PT, and TT maps are generated and displayed, but an operator can select arbitrary one type or two types.

These numeric values tend to appear as high values as compared with those of other tissues in the cerebral artery. Therefore, by a color display through a color lookup table set to display only the pixels having values centering on the value, the place of the cerebral artery can easily be identified, and the cerebral artery ROI can correctly be set (S5). Typically, in each of the left and right hemispheres, the cerebral artery ROI is set to three places of the anterior cerebral artery (ACA), medial cerebral artery (MCA), and posterior cerebral artery (PCA).

Furthermore, with multi-slice scanning, for example, when four slices disposed adjacent to one another are analysis objects, as shown in FIG. 11, the setting of the individual cerebral artery ROIs for the respective slices is not only large in an operation burden but also an unnecessary operation in performing the analysis. Therefore, the cerebral artery ROI set in a certain arbitrary one slice is also used in other slices. Moreover, a coherent regression method described later may also be used to prepare the time-density curve Ca(t) of the cerebral artery which can be used in common to all the slices.

Subsequently, the time-density curve preparation section 122 prepares the time-density curve Ca(t) from continuous image data by dynamic CT with respect to each set cerebral artery ROI (S6).

Here, there are many cerebral arteries which are very thin as compared with the pixel size. Additionally, in general, the cerebral artery does not cross perpendicular to the scanning slice of CT. Therefore, any pixel on the image does not correctly indicate the CT number of artery blood, one pixel is constituted by mixed presence of the cerebral artery and other tissues, and only a lower contrast enhancement effect is indicated because of a partial volume effect in most cases. Moreover, in these pixels including the arbitrary as a partial volume, an image noise is large. Particularly since the contrast enhancement effect is remarkably small in the artery of a portion with cerebral infarction caused therein, the influence of noise is enormously large. The image noise is suppressed by the above-described coherent filter, but the influence of the partial volume effect still remains.

For the time-density curve of the cerebral artery, instead of measuring the curve in a single slice image, the pixels in a solid including the artery are used to apply the coherent regression method described later, so that the problem can be solved. Therefore, instead of the above-described coherent filter method, the coherent regression method may also be applied in this stage.

Moreover, according to this method, the time-density curve of only one slice image corresponding to each artery is obtained, and therefore the curve can be used in analyzing the arbitrary portion in all the slices within the scan volume. Thereby, with respect to the specific artery, the slice by which the time-density curve of the cerebral artery is most clearly obtained is selected, the time-density curve of the cerebral artery can be applied to all the slices, and the number of time-density curves of the cerebral artery can be reduced.

(Coherent Regression Method)

When the time-density curve is prepared, it is important to remove the influences of the partial volume effect and random noise. First, the "time-density curve" is a curve indicating a change of the CT number (density value) in the specific portion of the dynamic CT image with elapse of time. Particularly, in the above-described medical image diagnosis apparatus, for a purpose of checking details of local blood flow circulations and metabolic functions in human body tissues, the change of the contrast medium concentration in the specific tissue of the human body with time has been measured as the time-density curve. Moreover, in astronomic observation, for a purpose of analyzing a luminous change of a specific celestial body, the time-density curve is used. The curve will more formally and clearly be described. That is, the time-density curve is represented as a pair of sequences $\{<t_k, d_k> (k=1, 2, \ldots, K)\}$, where the density value of a certain portion in time $t_k$ is $d_k$. Moreover, in many uses of the time-density curve, an absolute value of $d_k$ is not necessarily required, and it is rather sufficient to obtain only an increment $(d_k-d_1)$ in which the first image 1 is used as a reference. Furthermore, in many of the uses, it is sufficient to obtain only data $A(d_k-d_1)$ (here A is an unknown constant) which is simply proportional to $(d_k-d_1)$. Therefore, in this case, the pair of sequences $\{<t_k, A(d_k-d_1)> (k=1, 2, \ldots, K)\}$ is a required time-density curve.

To obtain the time-density curve, in principle, the scalar value $v_K(x)$ of the pixel x included in the portion in which the time-density curve is to be measured in the respective images k (k=1, 2, ..., K) constituting the dynamic CT image may be used to constitute the pair of sequences $\{<t_k, v_k(x)>\}$ or $\{<t_k, A(v_k(x)-v_1(x))>\}$.

However, in practical use, the dynamic CT image scanned by the medical image diagnosis apparatus includes the random noise, and therefore there is a problem that the time-density curve essentially to be measured cannot correctly be obtained.

Furthermore, in the practical use, in these dynamic CT images, a so-called "partial volume effect" is produced. The partial volume effect is a phenomenon in which the image of a micro material in the subject is represented by a small number of pixels on the image, but the small number of pixels are also influenced by the image of an adjacent material in the subject, and the pixel values of the small number of pixels (essentially in proportion to a fluctuation of the density value to be measured) indicate only a relatively small fluctuation. In other words, the pixel values of the small number of pixels include only a slight signal. Therefore, when the partial volume effect is produced, with any pixel x, the pair of sequences $\{<t_k, v_k(x)> (k=1, 2, \ldots, K)\}$ have a very low signal level, the pixel is influenced by the change of the density value in a tissue essentially not to be measured, and further the random noise exists. There is therefore a problem that the time-density curve $\{<t_k, d_k>\}$ to be essentially measured cannot correctly be obtained.

To solve the problem, the time or spatial smoothing has heretofore been used to suppress the random noise. However, with time average, the time resolution is impaired. Moreover, with the space averaging, there is a problem that the change with time of the density of the portion other than the portion essentially to be measured is mixed in the measured value. To solve the problem and obtain a more correct time-density curve, the coherent filter is used.

First, the null hypothesis which is to be used in the coherent filter of the present embodiment will be described. Assuming that a true time-density curve in the portion to be measured is $\{<t_k, d_k> (k=1, 2, \ldots, K)\}$, for a purpose of measuring a primary conversion $\{<t_k, A(d_k-d_1)> (k=1, 2, \ldots, K)\}$ (where A is an unknown coefficient), a set R of the pixels substantially corresponding to the portion to be measured is set. With respect to an arbitrary pixel x∈R as the element of the set R, on a condition Q that "the pixel x well reflects the above-described true time-density curve and is hardly influenced by the density change with time of another portion", with respect to the pixel value $v(x)=v_1(x), v_2(x), \ldots, v_K(x))$ as the vector value, in consideration of the partial volume effect and random noise influences, it can be assumed that the following is established.

$$v_k(x) = p(x)d_k + q(x) + \gamma_k(x) \quad (11)$$

(k=1, 2, ..., K)

Here, p(x) and q(x) are unknown coefficients which differ with each pixel x but do not change depending on an image number k (i.e., scan time $t_k$), and are modeled partial volume effects. Moreover, $\gamma_k(x)$ is a modeled random noise, the value differs with each pixel x and image number k, but the anticipated value is 0, and the statistic distribution does not depend on the pixel x or the image number k.

According to the above-described assumption, the following can be proved. If proposition "both the pixels x, y satisfy the above-described condition Q" is established with respect to two arbitrary pixels x, y as the elements of the set R, the following relation is established.

$$v_k(x) = a_1 v_k(y) + a_2 + \xi_k \ (k=1, 2, \ldots, K) \tag{12}$$

Here, $a_1$ and $a_2$ are unknown coefficients which differ with each pixel set x, y but do not change depending on the image number k (i.e., the scan time $t_k$). Moreover, $\xi_k$ is a random noise, the value differs with each pixel set x, y and image number k, but the anticipated value is 0.

The equation (12) is derived as follows.

$$v_k(y) = p(y) d_k + q(y) + \gamma_k(y) \tag{13}$$

That is, when the above equation obtained by assigning y to x is modified the following equation is obtained.

$$d_k = \frac{v_k(y) - q(y) - \gamma_k(y)}{p(y)} \tag{14}$$

When this is assigned to equation (20), the following is obtained.

$$v_k(x) = \frac{p(x)}{p(y)} v_k(y) + \left(q(x) - \frac{p(x)}{p(y)} q(y)\right) + \left(\gamma_k(x) - \frac{p(x)}{p(y)} \gamma_k(y)\right) \tag{15}$$

Therefore, with the following equation, the equation (12) is derived.

$$\left.\begin{array}{l} a_1 = \dfrac{p(x)}{p(y)} \\[4pt] a_2 = q(x) - \dfrac{p(x)}{p(y)} \\[4pt] \xi k = \gamma_k(x) - \dfrac{p(x)}{p(y)} \gamma_k(y) \end{array}\right\} \tag{16}$$

Here, $a_1$ and $a_2$ of the equation (16) are parameters indicating the partial volume effect, and $\xi_k$ of the equation (16) indicates a random noise.

The above has shown that the proposition "both the pixels x, y satisfy the condition Q" is equivalent to a null hypothesis $H_0'$ "$v_K(x) = a_1 v_k(y) + a_2 + \xi_k$ (k=1, 2, ..., K)".

A method of converting the null hypothesis $H_0'$ "$v_K(x) = a_1 v_k(y) + a_2 + \xi_k$ (k=1, 2, ..., K)" to a substantially equivalent proposition of a form which can actually be verified will next be described. To strictly mathematically represent the null hypothesis anew, the null hypothesis $H_0'$ indicates that "with the presence of certain constants $a_1$ and $a_2$, $\xi_k = v_K(x) - a_1 v_k(y) - a_2$ (k=1, ..., K) follows a normal distribution with a mean of 0 and dispersal of $(\sigma^2 h(a_1))$". Here, the coefficient $h(a_1)$ is as follows.

$$h(a_1) = 1 + a_1^2 \tag{17}$$

The equation (17) is quickly derived from the equation (16) indicating the definitions of $a_1$ and $\xi_k$, and general properties of the dispersal concerning a random variable. Moreover, the value of the above-described dispersal $\sigma^2$ can simply be estimated sufficiently for practical use.

As described above, if the constants $a_1$ and $a_2$ can be determined, it is possible to verify the above-described null hypothesis $H_0'$. Moreover, in actual, it is sufficient to obtain optimum estimated values $a_1^\sim$ and $a_2^\sim$ of these constants.

A known fitting method can be used as such in calculating the optimum estimated values of the constants $a_1$ and $a_2$. Then, as a typical concrete method of the fitting method, an outline in the use of a linear minimum square method will be described. To apply the linear minimum square method to the present embodiment, assuming that simply the square sum of $\xi_k$ in the null hypothesis is S(a), the following is defined.

$$S(a) \sum_{k=1}^{K} \{v_k(x) - a_1 v_k(y) - a_2\}^2 \tag{18}$$

The value of S(a) depends on a constant vector $a = (a_1, a_2)$, that is, the values of the constants $a_1$ and $a_2$. With calculation of the constant vector a in which S(a) indicates the minimum value, the optimum estimated values $a_1^\sim$ and $a_2^\sim$ can be obtained with respect to the constants $a_1$ and $a_2$ in the meaning of an unbiased estimate. Furthermore, as a concrete calculation method of the linear minimum square method, various known methods can be used. In addition, these known calculation methods are all very simple, and required calculation time is very small.

The optimum estimated values $a_1^\sim$ and $a_2^\sim$ of the constants $a_1$ and $a_2$ are calculated in this manner. As a result, the residual errors error defined by the following equation can concretely be calculated.

$$r_k^\sim(x,y) = v_K(x) - a_1^\sim v_k(y) - a_2^\sim \tag{19}$$

Therefore, this residual errors error $r_k^\sim$ can be used to rephrase the above-described null hypothesis $H_0'$ as a substantially equivalent null hypothesis $H_0''$ "$r_k^\sim(x,y)$ (k=1, 2, ..., K) follows a normal distribution with a mean of 0 and dispersal of $(1+(a_1^\sim)^2)\sigma^2$". This is a concrete proposition by which verification calculation can actually be executed.

Furthermore, the following representation by vector is introduced:

$$\left.\begin{array}{l} a^\sim = (a_1^\sim, a_2^\sim) \\ \xi = (r_1^\sim, \ldots, r_K^\sim) \end{array}\right\} \tag{20}$$

wherein the vectors a and $\xi$ depend on the set of pixels x, y.

$$f(a^\sim, v(y)) = a_1^\sim v(y) + a_2^\sim \tag{21}$$

Moreover, a vector value function f defined by the above equation is used to rephrase the null hypothesis $H_0'$ as the null hypothesis $H_0''$ "$v(x) = f(a^\sim, v(y)) + \xi$ (however, $\xi$ follows a normal distribution with a mean of 0 and dispersal of $(1+(a_1^\sim)^2)\sigma^2$)", and this is the same form as that of the above-described null hypothesis $H_0$. That is, it is apparent that the present embodiment is one modification example of the coherent filter. Here, the $f(a^\sim, v(y))$ means that the parameter a indicating the partial volume effect is adjusted to be optimum and the pixel value v(y) of the pixel y is converted so as to have a highest fidelity with the pixel value v(x) of the pixel x.

A method of obtaining the time-density curve using the null hypothesis $H_0''$ by the coherent filter in the present embodiment will next be described. For the set R generally corresponding to the portion to be measured, with respect to a certain one pixel x∈R included in the set R, the following calculation is performed with respect to all pixels y∈R as the elements of the set R. That is, the above-described method is used to actually calculate residual errors error $r_k^\sim(x,y)$ (k=1, . . . , K). Subsequently, a risk rate p(x,y) and weight w(p(x,y)) are concretely calculated for rejecting the above null hypothesis $H_0$," "$r_k^\sim(x,y)$ (k=1, . . . , K) follows a normal distribution with a mean of 0 and dispersal of $(1+(a_1^\sim)^2)\sigma^2$". Moreover, a weighted mean $v'_k(x)$ is calculated by the following equation (22), and the time-density curve in the pixel x $\{<t_k, v'_k(x)-v'_1(x)> (k=1, 2, \ldots, K)\}$.

$$v'(x) = \frac{\sum_{y \in R} w(p(x, y)) f(a^\sim, -v(y))}{\sum_{y \in R} w(p(x, y))} \quad (22)$$

The time-density curve obtained in this manner indicates a measured value which approximates primary conversion $\{t_k, A(d_k-d_1)>\}$ (wherein A is an unknown coefficient) of the true time-density curve in the pixel x $\{<t_k,d_k>\}$. In addition, the random noise is suppressed by the effect of the weighted mean. Moreover, with respect to the pixel value vector of another pixel y, as apparent from the equation, the curve in which the influence of the partial volume effect is corrected is used. Furthermore, the present invention has the common characteristic of the coherent filter "the time mean is not used, and the space mean is calculated using the weight based on the fidelity with the pixel x" as a property. Therefore, according to the present embodiment, the time-density curve can be obtained in which the influence of the partial volume effect is suppressed without impairing the time resolution and the random noise is suppressed. Additionally, a method of obtaining the time-density curve in this manner is referred to particularly as the "coherent regression method".

One example of clinical use of the time-density curve will next concretely be described in the dynamic CT image obtained by the dynamic CT scan in medical X-ray CT. In this application example, while the contrast medium is rapidly injected into the vessel, the scan such as dynamic CT is performed, the density change of the image of the artery existing in the human body tissue is measured as the time-density curve, and the blood flow circulation in the tissue is diagnosed.

In this application example, in many cases, since the artery in the human body tissue is generally very thin, the image of the artery appearing on a tomography image by CT produces the partial volume effect. Furthermore, needless to say, the image contains the random noise. Therefore, it is difficult to obtain a sufficiently correct time-density curve concerning the artery in the conventional method. When measurement is forcedly performed, only a measured value $<t_k, (v_k(x)-v_1(x))>$ is obtained. The value approximates to a certain degree the pixel value $<t_k, A(D_k-D_1)>$ (here $D_k$ indicates the pixel value (as the scalar value) of a group of pixels corresponding to the image of the artery in time $t_k$ k=1, 2, . . . , K) as the primary conversion of the true time-density curve $<t_k,D_k>$ concerning the artery. This measured value contains the random noise. Moreover, because of the influence of the partial volume effect, the coefficient A remains to be unknown.

Then, it is possible to obtain the measured value $<t_k,(v'_k(x)-v'_1(x))>$ (k=1, 2, . . . , K) which sufficiently approximates $<t_k,A(D_k-D_1)>$. On the other hand, a remarkably thick vein exists among the veins which can be observed on the same tomography image. Therefore, with respect to the veins, in the conventional method, a sufficiently good approximate value $<t_k,(J_k-J_1)>$ (k=1, 2, . . . , K) of the time-density curve can be obtained. Here, $J_k$ indicates the pixel value of one group of pixels corresponding to the image of the vein in time $t_k$.

Furthermore, in the time-density curve concerning the blood circulation, it is known that proposition S: "if the contrast medium concentration in the blood in time $t_1$, any time-density curve $<t_k,(d_k-d_1)>$ concerning any vessel d is matched in an area under curve (AUC)" is established as the property. Here, the area under curve means integration with respect to the time t of the time-density curve $<t_k,(d_k-d_1)>$.

Therefore, the area under curve AUC(d) of the time-density curve $<t_k,(d_k-d_1)>$ concerning the certain vessel d can approximately be calculated, for example, by the following equation.

$$AUC(d) \doteq \sum_{k=1}^{K-1} \frac{\{(d_{k+1}-d_1)+(d_k-d_1)\}(t_{k+1}-t_k)}{2} \quad (23)$$

Therefore, the area under curve AUC(J) concerning the time-density curve $\{<t_k,(J_k-J_1)>\}$ obtained with respect to the vein in the conventional method can be calculated using equation (22). J may be assigned to d. Moreover, if the time-density curve $\{<t_k,(D_k-D_1)>\}$ is known with respect to the artery, the area under curve AUC(D) can similarly be calculated using the equation (18). Additionally, according to the proposition S, the following must be established.

$$AUC(D) \cong AUC(J) \quad (24)$$

However, in actual, since the time-density curve $\{<t_k,(D_k-D_1)>\}$ is unknown, AUC(D) cannot be calculated.

On the other hand, the time-density curve $<t_k,(v'_k(x)-v'_1(x))>$ obtained in the method according to the present embodiment approximates $<t_k,A(D_k-D_1)>$, and the latter contains the unknown coefficient A. Therefore, an area under curve AUC(v') which can concretely be calculated from $\{<t_k, (v'_k(x)-v'_1(x))>\}$ using the equation (23) has to be just A times the area AUC(D). That is, the following results.

$$AUC(v') \cong A \, AUC(D) \quad (25)$$

That is, from the equations (24) and (25), the following relation is established.

$$A \cong AUC(v')/AUC(J) \quad (26)$$

The right side of the equation (26) can concretely be calculated using the equation (23), and therefore the value of the coefficient A which has been unknown can concretely be determined. Then, when this value of the coefficient A is used to constitute the time-density curve $<t_k,(v'_k(x)-v'_1(x))/A>$, this is nothing but approximation of the time-density curve $<t_k,(D_k-D_1)>$ of the artery. A method of using the area under curve to constitute the time-density curve having the determined value of the proportional coefficient A which has been unknown is referred to as an "AUC method".

Therefore, the AUC method is further combined with the coherent regression method in the clinical use of the time-density curve in the dynamic CT image obtained by the dynamic CT scan, thereby the influences of the partial volume effect and random noise are removed, and the measured value including no unknown proportional coefficient A is obtained even with respect to the time-density curve of a thin artery. The measurement of the curve has been difficult or impossible in the conventional method.

Furthermore, of course, the AUC method can also be applied to the time-density curve $<t_k,(v'_k(x)-v'_1(x))>$ concerning the artery singly measured by the conventional method. The influences of the random noise and partial volume effect cannot be removed, but the time-density curve having the determined value of the proportional coefficient A which has been unknown can be constituted.

(Correction of Time Density Curve of Cerebral Artery Using Time Density Curve of Upper Sagittal Sinus Venosus (Suppression of Influence of Partial Volume Effect))

In order to suppress the influence of the partial volume, instead of or in addition to the coherent regression, the time-density curve Csss(t) of the upper sagittal sinus venosus may be used to correct the time-density curve Ca(t) of the cerebral artery.

First, in step S7 of FIG. 5, as shown in FIG. 12, a slightly large upper sagittal sinus venosus ROI is set so as to surround the upper sagittal sinus venosus on the CT image. Since the upper sagittal sinus venosus is large as compared with the artery and the position thereof is relatively fixed, it is easy to set the upper sagittal sinus venosus ROI. This slightly large upper sagittal sinus venosus ROI includes a plurality of pixels.

Subsequently, the upper sagittal sinus venosus ROI is reduced/processed so that all the pixels of the upper sagittal sinus venosus ROI are included in the upper sagittal sinus venosus over the whole area (S8). For example, the reduction processing includes: first executing a threshold value processing (binarization) with respect to each of the pixels in the upper sagittal sinus venosus ROI; and preparing a binary map in the ROI ("0", "1"). The threshold value is set to a value which separates the image of the upper sagittal sinus venosus from the image of the peripheral tissue and bone. "1" indicates the pixel on the image of the upper sagittal sinus venosus, and "0" indicates the pixel on the image of the peripheral tissue and blood. Each pixel (center pixel) of the binary map is replaced in accordance with the values of four or eight pixels in the vicinity. Only when the center pixel is "1", and all the four or eight pixels in the vicinity are "1", the value of the center pixel is maintained at "1". That is, of course when the center pixel is "0", even when the pixel is "1", and also when any one of the four or eight pixels in the vicinity indicates "0", the value of the center pixel is replaced with "0". Therefore, the upper sagittal sinus venosus ROI is reduced by at least one pixel as compared with the outer shape of the image of the upper sagittal sinus venosus. Thereby, a condition that all the pixels in the upper sagittal sinus venosus ROI subjected to the reduction processing are pixels on the upper sagittal sinus venosus image can be realized with high degree of certainty.

Moreover, instead of this technique, the area under curve AUC of the time-density curve may be used to correct the upper sagittal sinus venosus ROI. In this case, the slightly large ROI is used as a search range, and the area under curve AUC of the time-density curve is calculated with respect to each of the pixels in the range. By the contrast enhancement effect, the area under curve AUC of the pixel on the upper sagittal sinus venosus image apparently indicates a high value as compared with the value of the peripheral pixel. Therefore, when the threshold value processing is executed with respect to the area under curve AUC, only the pixel on the upper sagittal sinus venosus image can be selected from the ROI.

With respect to a plurality of pixels having a high degree of certainty that the pixels are on the upper sagittal sinus venosus image picked up by AND condition using any or both of the techniques in this manner, the time-density curve of each pixel is averaged, and the time-density curve Csss(t) of the upper sagittal sinus venosus is prepared (S9).

Figure 13:
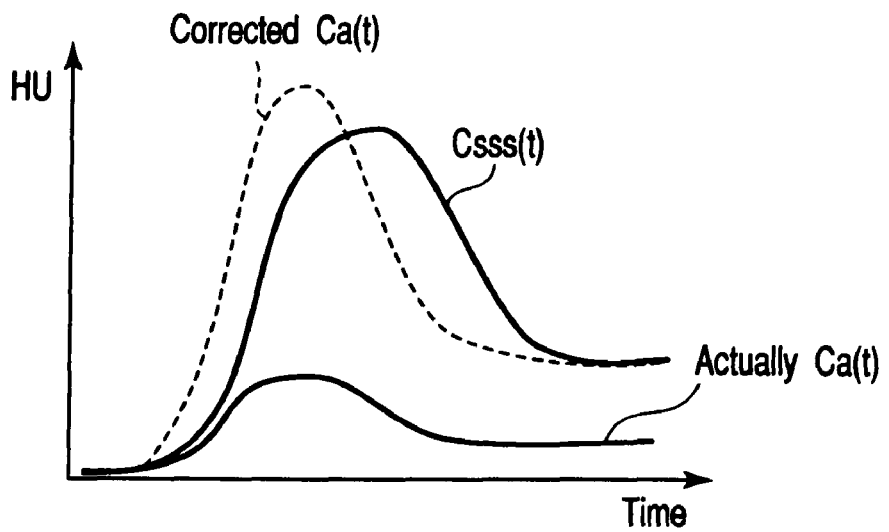
FIG. 13 is a supplementary diagram concerning correction of a time-density curve of the cerebral artery of step S10 of FIG. 5.

Here, since the iodinated contrast medium does not pass through a blood brain barrier, in principle, iodine concentration does not change with the cerebral artery and vein. That is, the area under curve AUC of the time-density curve Csss(t) of the upper sagittal sinus venosus is almost equivalent to the area under curve AUC of the time-density curve Ca(t) of the cerebral artery prepared in S6. Therefore, as shown in FIG. 13, the time-density curve Ca(t) is corrected by multiplying each time value of the time-density curve Ca(t) of the cerebral artery prepared in S6 by AUC(sss/AUCa) so that the area under curve AUCa of the time-density curve Ca(t) of the cerebral artery prepared in S6 is almost equivalent to the area under curve AUCsss of the time-density curve Csss(t) of the upper sagittal sinus venosus (S10).

Subsequently, the time-density curve Ca(t) of the cerebral artery shown in FIG. 14A in which the noise and partial volume effect are suppressed as described above is used to quantize the state of the blood flow circulation for the cerebral tissue (capillary). For this, the time-density curve Ci(t) shown in FIG. 14B is first prepared with respect to each pixel on the cerebral tissue (S11).

Subsequently, as shown in S12, the separate cerebral artery time-density curves Ca(t) are used for the left and right areas, and the cerebral artery time-density curve Ca(t) is used as the input function and the time-density curve Ci(t) for the cerebral tissue is used as the output function for each pixel to obtain the characteristics of process of passage of the tracer through the capillary as the modulation transfer function MTF. That is, with respect to the time-density curve Ci(t) for the cerebral tissue of the left area, the time-density curve Ca(t) of the cerebral artery of the same area is used. Moreover, with respect to the time-density curve Ci(t) for the cerebral tissue of the right area, the time-density curve Ca(t) of the cerebral artery of the same right area is used to obtain the modulation transfer function MTF. Furthermore, since the cerebral artery time-density curve Ca(t) is prepared for each of ACA, MCA, PCA as described above, the calculation of the modulation transfer function MTF is repeated every Ca(t).

Figure 15:
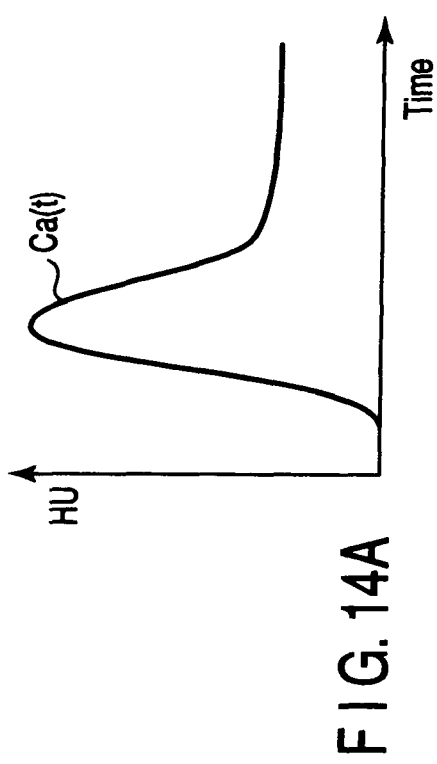
FIG. 15 is a principle explanatory view of a box-MTF method of step S12 of FIG. 6.

Here, as shown in FIG. 15, an ideal relation established between the time-density curve Ca(t) of the cerebral artery and the time-density curve Ci(t) of the capillary is used as an analysis model to apply a box-MTF method.

FIG. 16 shows a principle of the box-MTF method. The method includes: evaluating a residual errors error between a convolution Ci'(t) of the time-density curve Ca(t) of the cerebral artery with a modulation transfer function box-MTF represented by a rectangular function and actual measurement Ci(t) prepared in S11; and correcting the modulation transfer function box-MTF so as to reduce a square sum of the residual errors error. This procedure routine is repeated to minimize the residual errors error.

Figure 14A:
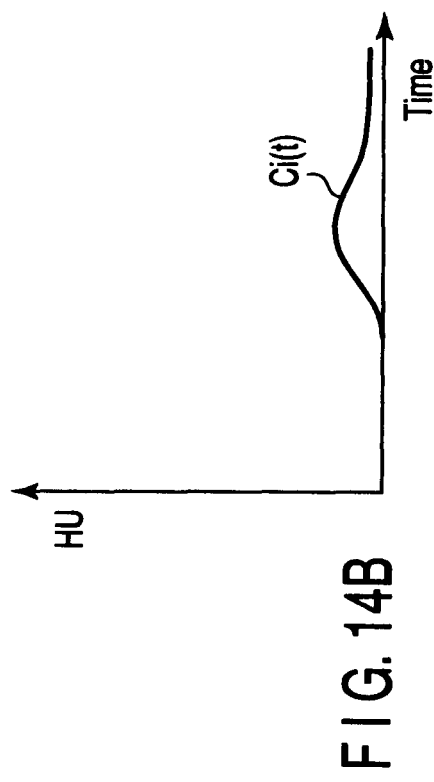
FIGS. 14A, 14B show one example of a time-density curve $Ca(t)$ of the cerebral artery and time-density curve $Ci(t)$ for the cerebral tissue prepared in steps S10, S11 of FIG. 5.
Figure 14B:
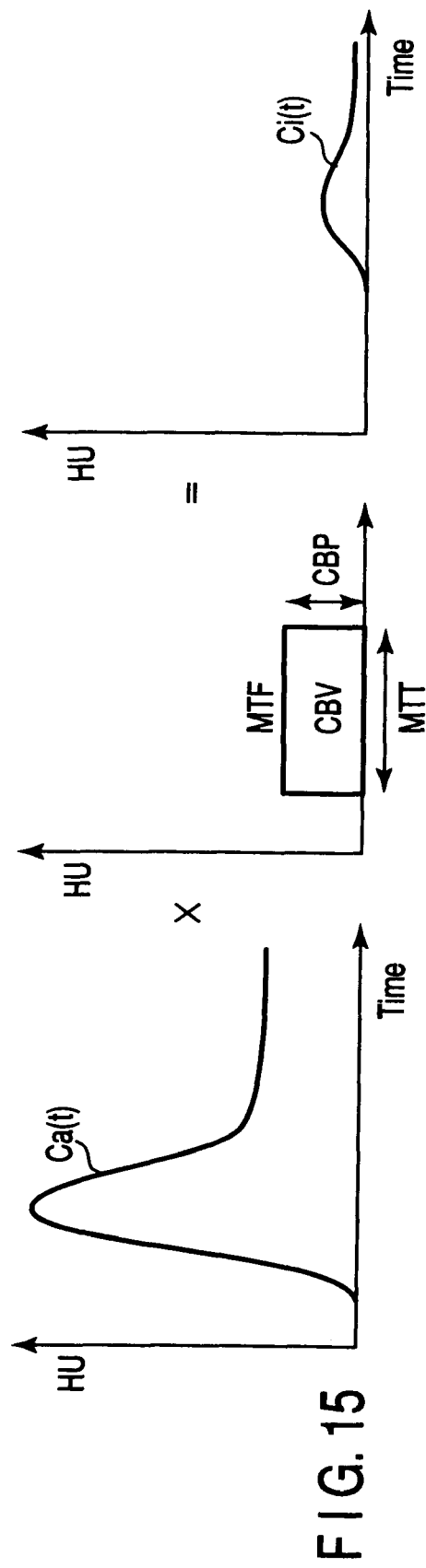
Figure 18A:
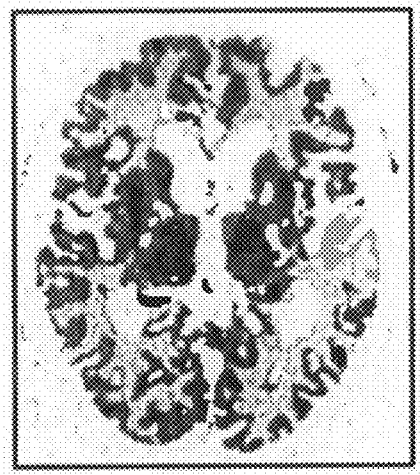
FIGS. 18A to 18D are diagrams showing one example of each map of CBP, CBV, MTT, Err prepared in step S16 of FIG. 6.
Figure 18B:
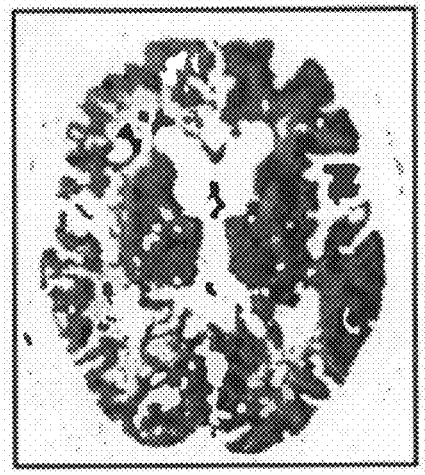
Figure 18C:
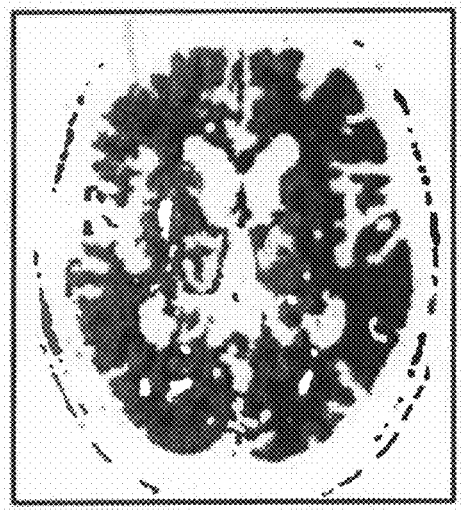
Figure 18D:
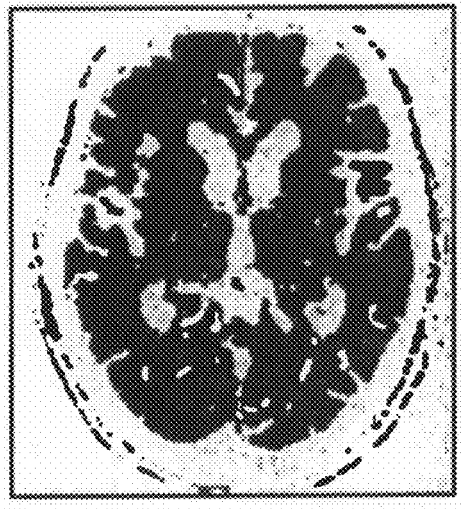

As shown in FIGS. 14A and 14B, CBP, CBV, MTT are calculated based on the modulation transfer function box-MTF which minimizes the residual errors error (S13), and the square sum of the residual errors error minimized in S12 is output as Err. Strictly, the correction is performed with the following.

$$CBP=CBP$$

$$CBV=(1-Ht)/(1-b*Ht)*CBV'$$

$$MTT=(1-Ht)/(1-b*Ht)*MTT'$$

Here, Ht is a hematocrit value of a major vessel, and b*Ht is a hematocrit value of a peripheral vessel (generally b is about 0.7).

Furthermore, the residual errors error is given by $y_i(x)-f(t_i,x)$. $y_i(x)$ indicates the scalar value of a box cell x in time $t_i$, and corresponds to the time-density curve for the cerebral tissue. $f(t_i,x)$ indicates the scalar value in the time $t_i$ of a model fitted to the vector pixel value of the box cell x, and corresponds to the convolution of the modulation transfer function with the time-density curve of the cerebral artery. Err is a square root of the square sum of the residual errors error in approximating the modulation transfer function, and calculated, for example, as represented by the following equation.

$$Err = \sqrt{\frac{\sum_{i=1}^{N}(y_i(x)-f(t_i,x))^2(w(t_i))^2}{S}}$$

Here, S is a constant, and for example S=N−p. p denotes a degree of freedom, that is, the number of parameters included in an approximated model f. $w(t_i)$ is a weight coefficient which determines a degree of contribution of the residual errors error in the time $t_i$ to Err. For example, $w(t_i)$ does not have to depend on i, and may have a fixed value such as 1. Alternatively, $w(t_i)=\alpha e^{-t^2/\beta}$ is also acceptable which is constituted so that the weight w moderately decreases with an increase of $|t_i|$. With an elapse of time, the residual errors error does not have to contribute much to Err.

With respect to CBP, CBV, MTT, Err calculated from the modulation transfer function obtained by the box-MTF method in this manner, as shown in FIG. 17, individual output ranges (appropriate ranges) are set (S14). With respect to the pixels having the values of the corresponding output ranges, the values are maintained. For the pixels having values outside the output range, the values are replaced, for example, with values corresponding to black on the display (S15).

Figure 19:
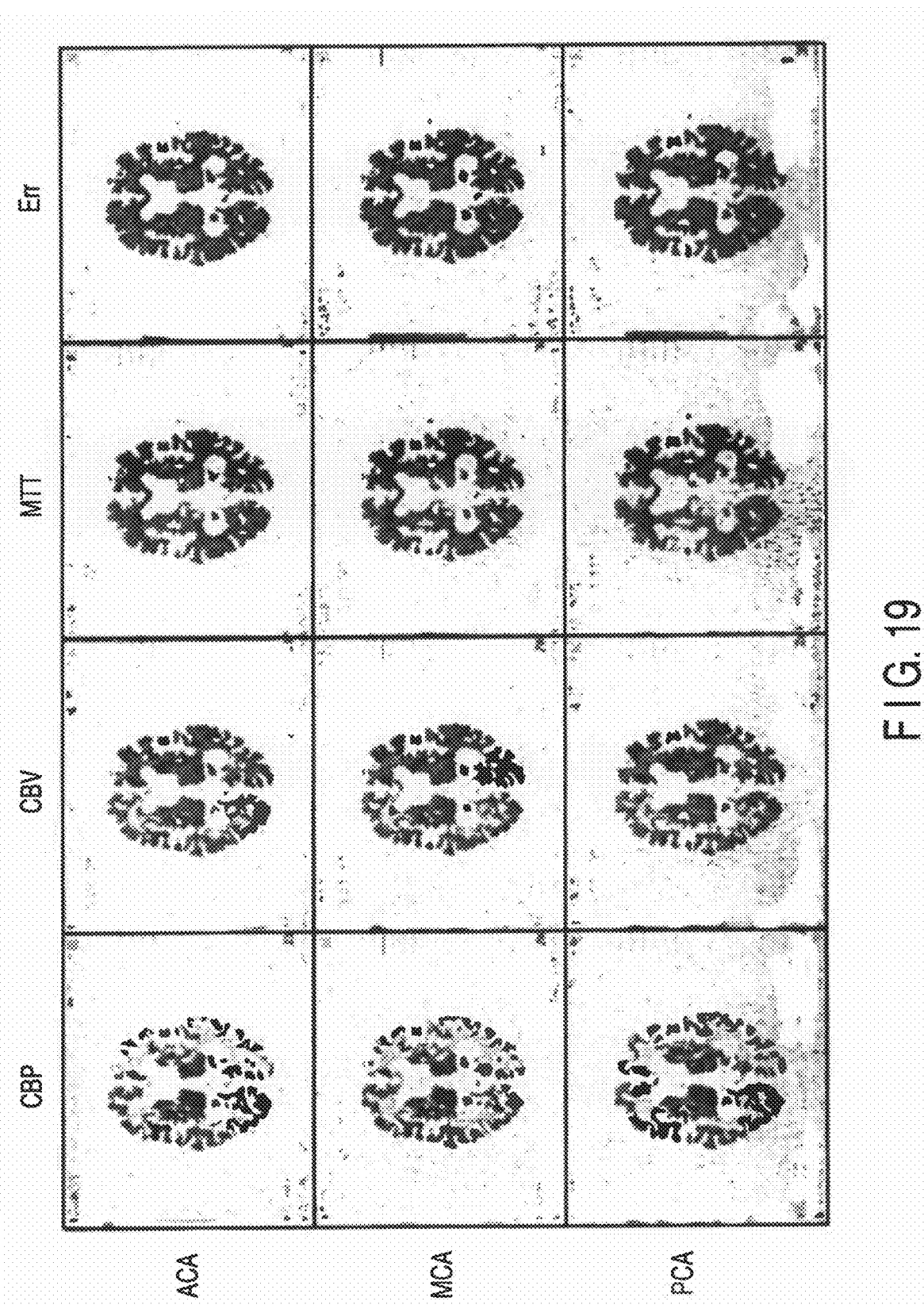
FIG. 19 is a diagram showing a list of the CBP, CBV, MTT, and Err maps prepared for each cerebral artery in the step S16 of FIG. 6.

Subsequently, as shown in FIGS. 18A to 18D, the respective maps are generated from CBP, CBV, MTT, Err subjected to output optimization (S16). The indices of the CBP, CBV, MTT, Err are individually calculated for the respective slices with respect to the anterior cerebral artery ACA, medial cerebral artery MCA, and posterior cerebral artery PCA. Therefore, even with one slice, 4×3=12 maps are obtained as shown in FIG. 19. When the number of cerebral arteries to be set is increased, the maps increase to the number four times the increase number of arteries. It is not realistic to generally evaluate such many maps. Then, in order to reduce the number of maps, the maps are synthesized (S17).

Figure 20:
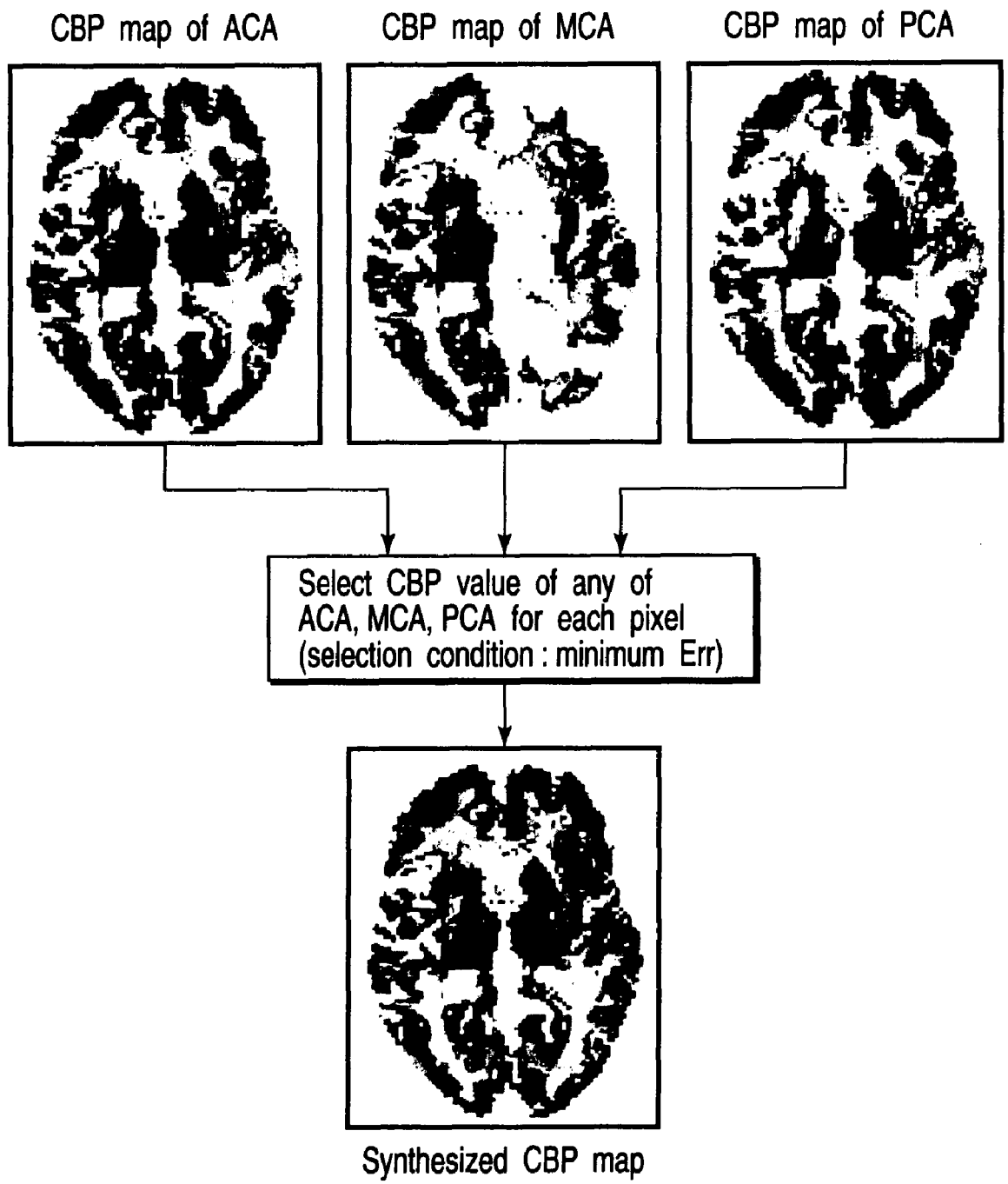
FIG. 20 is an explanatory view of a map synthesis method of step S17 of FIG. 6.

As shown in FIG. 20, synthesis method includes: synthesizing the CBP maps of the anterior cerebral artery ACA, medial cerebral artery MCA, and posterior cerebral artery PCA based on the residual errors Err of anterior cerebral artery ACA, medial cerebral artery MCA, and posterior cerebral artery PCA. For example, when the modulation transfer function MTF is obtained from the time-density curve Ca(t) of the anterior cerebral artery ACA and the time-density curve Ci(t) for the cerebral tissue under the control, the residual errors error Err is relatively small. Conversely, when the modulation transfer function MTF is obtained from the time-density curve Ci(t) for the cerebral tissue not under the control, the residual errors error Err is relatively large. That is, the residual errors error Err indicates a control possibility of each cerebral artery.

Therefore, for each of the pixels, the CBP value corresponding to a lowest value of residual errors error Err is selected as the value of the pixel from the CBP values of the anterior cerebral artery ACA, medial cerebral artery MCA, and posterior cerebral artery PCA. The map synthesized in this manner is constituted of the CBP value for the cerebral tissue having a high possibility of being under the control of the anterior cerebral artery ACA, medial cerebral artery MCA, and posterior cerebral artery PCA. This also applies to the map synthesis of the other indices CBV, MTT.

Here, the map synthesis will be described hereinafter in detail. The time-density curve obtained from the pixel existing in the position corresponding to the artery reflects a contrast medium concentration in artery blood, and the above-described coherent regression method is applied, so that the time-density curve of a correct artery blood contrast medium concentration can be obtained. Such time-density curve of the cerebral artery can be prepared for each artery, and differs depending on a blood circulation state. Particularly, in a case of cerebral vascular disorder, the difference is sometimes remarkable. For example, the time-density curve of the cerebral artery obtained in the arteries of K places is represented by $A_k(t)$ (k=1, 2, ..., K).

When the time-density curve of a certain tissue is compared with the time-density curve of the cerebral artery of the artery which nourishes (controls) the tissue, it is possible to obtain the index such as CBP reflecting micro circulation (structure, function of a capillary system) in the tissue. Since these indices are calculated for each portion (x,y,z), the image can be constituted with the value as the pixel value, and this image is an index map. For example, when R types (typically four types of CBP, CBV, MTT, Err as described above) of indices are obtained, R maps can be constituted. R maps prepared in this manner can be regarded as one map (vector value map) in which each pixel has a vector value. That is, the following results.

$$V_k(x,y,z)=<P_{k,1}(x,y,z),P_{k,2}(x,y,z),\ldots,P_{k,R}(x,y,z)>$$

For example, in the CBP study, typically R=4 is set as described above, and $P_{k,1}(x,y,z)$ can be constituted to indicate the value of CBP, $P_{k,2}(x,y,z)$ to indicate the value of CBV, $P_{k,3}(x,y,z)$ to indicate the value of MTT, and $P_{k,4}(x,y,z)$ to indicate the value of residual errors error Err.

In the portion (x,y,z), a portion apparently not corresponding to an internal organ as the analysis object is excluded from the analysis object from the beginning, and a special value indicating the exclusion from the analysis object may be assigned to $P_{k,r}(x,y)$ (the steps S14, S15). To use a negative value whose absolute value is large as the value is convenient. Alternatively, as another element to be added to the vector $V_k(x,y,z)$, a map $P_{k,R+1}(x,y,z)=(0$ when (x,y,z) is excluded from the analysis object, otherwise 1) may also be prepared. This map is called a "mask".

This vector value map $V_k$ is prepared for each time-density curve $A_k$ of the referred cerebral artery. For example, if the time-density curve of the cerebral artery is obtained from left and right medial, anterior, posterior cerebral arteries, K=6. Furthermore, when the time-density curve of the cerebral artery is obtained from several arteries in the periphery of the affected area, K=about 10 to 15.

Therefore, the time-density curve of the cerebral artery obtained from the artery in a right hemisphere has to be used only in analyzing the portion (x,y,z) belonging to the right hemisphere, whereas the time-density curve of the cerebral artery obtained from the artery in a left hemisphere has to be used only in analyzing the portion (x,y,z) belonging to the left hemisphere. Then, an operator designates a boundary (median line) of the right and left hemispheres as a line, curve, bent line, plane, or curved surface, so that the map is preferably prepared for each hemisphere in the constitution. However, the number of time-density curves of the cerebral artery which can still exist in each hemisphere is K=about 3 to 10.

When the number K of the time-density curves $A_k$ (k=1, 2, ..., K) of the cerebral artery is large, the number of vector value maps $V_k$ (k=1, 2, ..., K) obtained as a result is large, and this is inconvenient for observation. That is, for the observation of a usual gray scale image or color scale image, one map is constituted of R images, there are K maps, and therefore K×R images in total have to be compared with one another. Furthermore, the portion nourished by the artery and the corresponding artery are not necessarily apparent, and anatomical knowledge has to be used to judge the map $V_k$ (k=1, 2, ..., K) to be observed for each portion. Particularly in the case of development of the cerebral vascular disorder such as cerebral infarction, the judgment of the artery which controls the tissue does not necessarily agree with the anatomical knowledge, and abnormal control is frequently seen. By these problems, there is a problem that it is difficult to interpret radiogram of the vector value map.

To solve the problem, the maps are synthesized. That is, the residual errors error map is used to put together K vector value maps $V_k$ (k=1, 2, ..., K) into one vector value map V. For example, when $P_{k,R}(x,y,z)$ is the residual errors error map, $V(x,y,z)=V_k(x,y,z)$, wherein k is such that $|P_{k,R}(x,y,z)|$ is minimized among k=1, 2, ..., K.

Moreover, a map $P_0(x,y,z)$=(k such that $|P_{k,R}(x,y,z)|$ is minimum among k=1, 2, ..., K) can be added to indicate k used in each portion among k=1, 2, ..., K.

According to this method, that is, during the observation of the usual gray scale image or color scale image, R or R+1 images may be observed.

According to the method, there is a possibility that a calculation result incorrectly using $A_k$ is used in the portion (x,y,z) to be essentially calculated using a time-density curve $A_j$ of the cerebral artery. However, to make such mistake, as apparent from the definition of V(x,y,z), a relation $|P_{k,R}(x,y,z)|<|P_{j,R}(x,y,z)|$ is necessary. This relation is established only when $A_j$ is remarkably similar to $A_k$. Therefore, it is considered that $V_k(x,y,z)$ is originally similar to $V_j(x,y,z)$ in the portion (x,y,z), and there is hardly possibility that a mistake is made in interpreting V(x,y,z) by this mistake.

When this method is actually applied, and only when $A_j$ is remarkably similar to $A_k$, in a tissue seemingly almost uniform, $P_0(x,y,z)$=k or $P_0(x,y,z)$=j depending on each portion. In this case, $P_{k,r}(x,y,z) \cong P_{j,r}(x,y,z)$ (r=1, 2, ..., R). It is observed that there is hardly difference even with the use of either value.

Conversely, with the tissue controlled by the specific artery, when the time-density curve $A_k$ of the corresponding cerebral artery is not similar to another curve, by the use of the present method, $V_k(x,y,z)$ is almost securely and automatically selected in the portion (x,y,z) in the tissue. Therefore, when the $P_0(x,y,z)$ is observed, the control in the tissue and the controlling artery can be observed without any anatomical knowledge.

Here, turning back to FIG. 6. As shown in FIGS. 21A to 21D, the region of interest ROI including a plurality of pixels is set with respect to the map synthesized as described above, or the single CBP, CBV, MTT, or Err map in each cerebral artery (S18), mean values (CBP, CBV, MTT, Err mean values) of the pixel values (CBP, CBV, MTT, Err values) in the ROI are calculated (S19), and the mean value is sometimes used as a diagnosis material. In this averaging, appropriate ranges are set for CBP, CBV, MTT, Err in the step S14, the value within the range is maintained, and the value out of the range is replaced with the minimum value corresponding, for example, to black representation. Therefore, the values including the replaced value are averaged, the mean value naturally includes an error. Therefore, for the averaging processing, it is necessary to select only the value in the appropriate range, or exclude the replaced value, and execute the averaging processing.

Moreover, to set the region of interest ROI for the averaging, when the region of interest ROI is set on any map of the CBP, CBV, MTT, Err maps, the ROI can be used in common to the other maps. An ROI setting operation is simplified, and it is also possible to calculate the mean value concerning the same ROI (CBP, CBV, MTT, Err mean values).

Here, as described above, the minimum residual errors error Err of the time-density curve of the certain tissue with respect to the time-density curve of the certain cerebral artery indicates a degree of control in the tissue by the cerebral artery, that is, a degree of blood flow supply to the tissue by the cerebral artery. In other words, the error indicates a degree in the tissue belonging to the cerebral artery, that is, a degree of blood flow supply to the cerebral tissue from the cerebral artery. The cerebral artery corresponding to the small residual errors error Err indicates a high control possibility with respect to the cerebral tissue of the pixel, and the cerebral artery corresponding to a large residual errors error Err indicates a low control possibility with respect to the cerebral tissue of the pixel. Therefore, it is possible to generate a map which distinguishes the cerebral artery having the high control possibility with a label for each pixel from the residual errors error Err, that is, a control map which distinguishes regions having the high control possibility of the anterior cerebral artery ACA, medial cerebral artery MCA, and posterior cerebral artery PCA.

Figure 22:
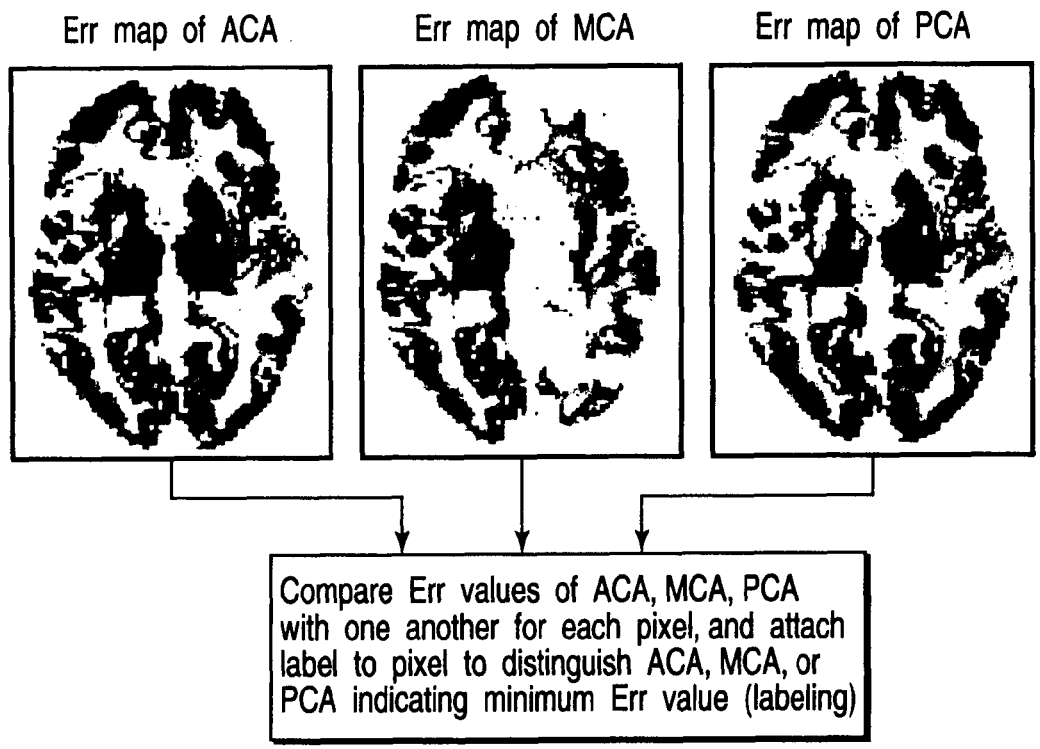
FIG. 22 is a diagram showing a generation method of a map (control map) in which cerebral arteries (ACA, MCA, PCA) having a high dominance possibility are distinguished by labels for each pixel (local tissue) in the step S17 of FIG. 6.

As shown in FIG. 22, with respect to the left and right areas of the brain, the residual errors Err of the anterior cerebral artery ACA, medial cerebral artery MCA, and posterior cerebral artery PCA are compared with one another for each pixel. It is indicated that the cerebral artery (ACA, MCA, or PCA) indicating a minimum residual errors error has a highest possibility of controlling the cerebral tissue of the pixel. For each pixel, the cerebral artery having the highest control possibility, that is, the minimum value of the residual errors error Err is specified. A label corresponding to the specified cerebral artery is given to each pixel.

Figure 24A:
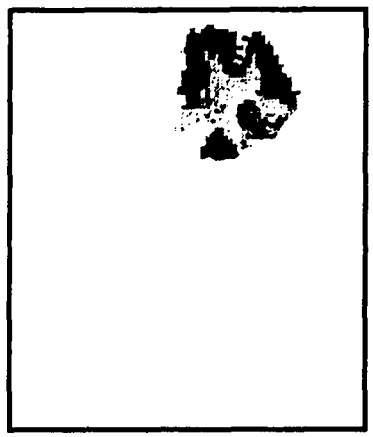
FIGS. 24A to 24C are diagrams showing the CBP map filtered using the control map.
Figure 24B:
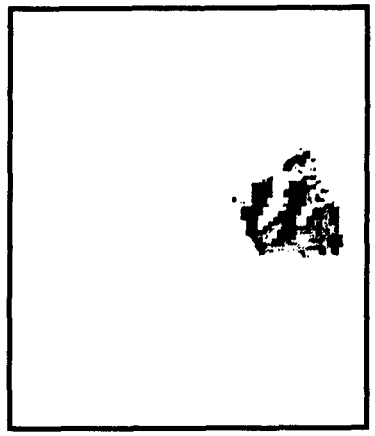
Figure 24C:
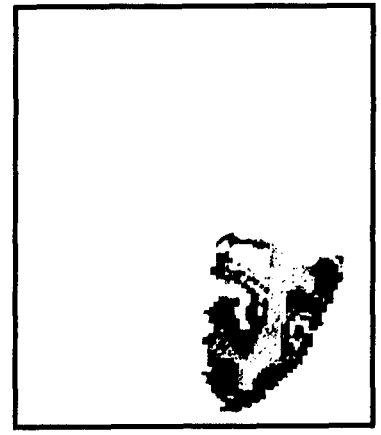
Figure 23:
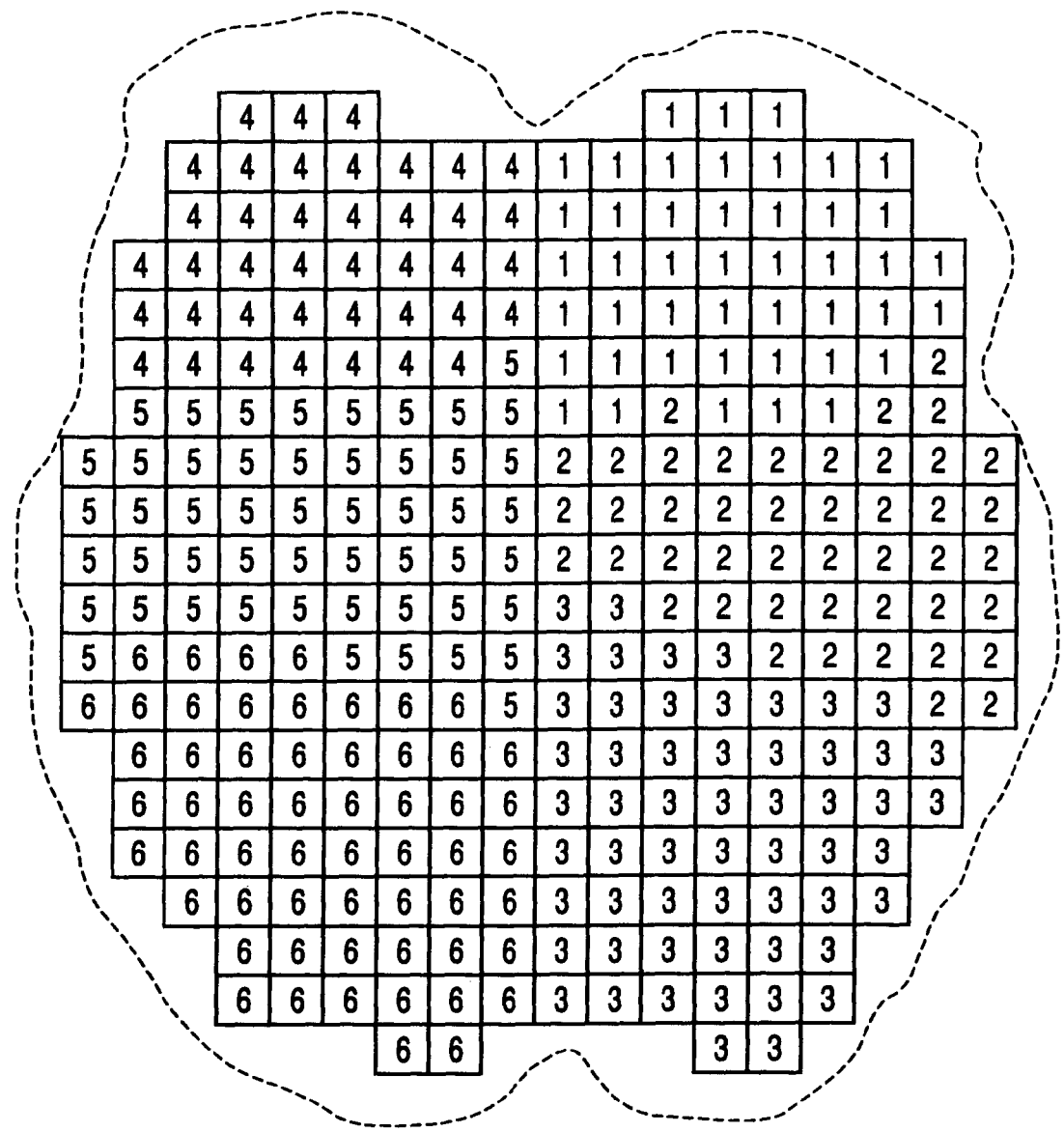
FIG. 23 is a diagram showing an example of the control map generated by the generation method of FIG. 22.

FIG. 23 shows an example of a generated control map. In this control map, the label is distinguished and displayed with color and shading. Moreover, when the index map is filtered with the arbitrary label, as shown in FIGS. 24A, 24B, 24C, it is possible to extract the region having the high control possibility from the index map for each cerebral artery (ACA, MCA, or PCA).

As described above, according to the present embodiment, by the coherent filter or coherent regression, the space and time resolutions are inhibited from dropping, and the noise is suppressed, so that the analysis precision of the CBP study can be enhanced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An index calculation method executed by an image processing apparatus, comprising:

using, at the image processing apparatus, a weight in accordance with a degree of similarity between pixels to filter a plurality of images in order to reduce noise from the plurality of continuous images concerning a specific region of a subject with a contrast medium injected therein, wherein the weight is a first weight for a first degree of similarity and the weight is a second weight greater than the first weight for a second degree of similarity higher than the first degree of similarity;

preparing, at the image processing apparatus, first time-density curves concerning arteries in the specific region and second time-density curves concerning tissues in the specific region from the plurality of images with the reduced noise;

calculating, at the image processing apparatus, modulation transfer functions indicating local blood flow circulations in the tissues with respect to the respective arteries by curve-fitting so that residual errors of the second time-density curves are minimized with respect to convolution of the modulation transfer functions and first time-density curves; and calculating, at the image processing apparatus, indices concerning the local blood flow circulations with respect to the respective arteries from the modulation transfer functions.

2. The method according to claim 1, further comprising:
determining the similarity between the pixels based on a difference of time-density curves between the pixels.

3. The method according to claim 1, further comprising:
determining the similarity between the pixels based on a difference of time-density curves between the pixels and a dispersal anticipated value of the noise.

4. The method according to claim 1, further comprising:
replacing each pixel value of the pixel constituting the image with a weighted average with a peripheral pixel by the weight.

5. The index calculation method according to claim 1, wherein the modulation transfer function is a rectangular function.

6. The method of claim 1, wherein the using comprises:

setting, for each of a plurality of pixels, a combination of vector values corresponding to values of said each pixel included in the plurality of images;

determining, by statistical testing, degrees of similarity of combinations of vector values corresponding to the plurality of pixels;

weighting values of pixels corresponding to combinations of vector values proportionally to the degree of similarity; and calculating an average of weighted pixel values in each of the plurality of images.

7. An index calculation apparatus comprising:

a filter section which uses a weight in accordance with a degree of similarity between pixels to filter a plurality of images in order to reduce noise from the plurality of continuous images concerning a specific region of a subject with a contrast medium injected therein, wherein the weight is a first weight for a first degree of similarity and the weight is a second weight greater than the first weight for a second degree of similarity higher than the first degree of similarity;

a time-density curve preparation section which prepares first time-density curves concerning arteries in the specific region and second time-density curves concerning tissues in the specific region from the plurality of images with the reduced noise;

a modulation transfer function calculation section to calculate modulation transfer functions indicating local blood flow circulations in the tissues with respect to the respective arteries by curve-fitting so that residual errors of the second time-density curves are minimized with respect to convolution of the modulation transfer functions and first time-density curves; and an index calculation section to calculate indices concerning the local blood flow circulations with respect to the respective arteries from the modulation transfer functions.

* * * * *